(12) United States Patent
Shimomura

(10) Patent No.: US 12,213,642 B2
(45) Date of Patent: Feb. 4, 2025

(54) ENDOSCOPE SYSTEM AND OPERATION METHOD THEREFOR

(71) Applicant: FUJIFILM Corporation, Tokyo (JP)

(72) Inventor: Koji Shimomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 30 days.

(21) Appl. No.: 17/815,052

(22) Filed: Jul. 26, 2022

(65) Prior Publication Data

US 2023/0037060 A1 Feb. 2, 2023

(30) Foreign Application Priority Data

Jul. 27, 2021 (JP) ................. 2021-122748

(51) Int. Cl.
| | |
|---|---|
| *A61B 1/045* | (2006.01) |
| *A61B 1/00* | (2006.01) |
| *A61B 1/05* | (2006.01) |
| *A61B 1/06* | (2006.01) |
| *A61B 1/07* | (2006.01) |
| *G02B 23/24* | (2006.01) |
| *G02B 23/26* | (2006.01) |
| *H04N 25/531* | (2023.01) |

(52) U.S. Cl.
CPC .......... *A61B 1/00009* (2013.01); *A61B 1/045* (2013.01); *A61B 1/0653* (2013.01); *A61B 1/0655* (2022.02); *G02B 23/2461* (2013.01); *G02B 23/26* (2013.01); *H04N 25/531* (2023.01)

(58) Field of Classification Search
None
See application file for complete search history.

(56) References Cited

U.S. PATENT DOCUMENTS

| | | |
|---|---|---|
| 2009/0268010 A1 | 10/2009 | Zhao et al. |
| 2016/0353972 A1 | 12/2016 | Yano et al. |
| 2018/0310829 A1 | 11/2018 | Frangioni et al. |
| 2019/0008372 A1 | 1/2019 | Tanaka et al. |
| 2021/0007575 A1* | 1/2021 | Kikuchi ............... G06T 7/0012 |
| 2021/0052161 A1 | 2/2021 | Tsukashima et al. |
| 2021/0145248 A1* | 5/2021 | Ito .................. A61B 1/000094 |
| 2022/0133140 A1 | 5/2022 | Kojima |
| 2023/0039047 A1* | 2/2023 | Fujii ............... A61B 1/000095 |

FOREIGN PATENT DOCUMENTS

| | | |
|---|---|---|
| JP | 2020-518349 A | 6/2020 |
| WO | 2015/136963 A1 | 9/2015 |
| WO | 2017/158906 A1 | 9/2017 |
| WO | 2020/170669 A1 | 8/2020 |

OTHER PUBLICATIONS

An Office Action; "Notice of Reasons for Refusal," mailed by the Japanese Patent Office on Dec. 3, 2024, which corresponds to Japanese Patent Application No. 2021-122748 and is related to U.S. Appl. No. 17/815,052; with English language translation.

* cited by examiner

*Primary Examiner* — Samuel D Fereja

(74) *Attorney, Agent, or Firm* — Studebaker & Brackett PC

(57) ABSTRACT

An endoscope system irradiates a subject with each of a plurality of pieces of illumination light in a preset order, images the subject according to a preset first imaging frame rate during a first period in which first illumination light included in the plurality of the illumination light is applied, acquires a first image captured during the first period, generates a first display image according to a first display frame rate higher than the first imaging frame rate on the basis of the acquired first image, and displays the first display image on a display.

15 Claims, 14 Drawing Sheets

ENDOSCOPE SYSTEM AND OPERATION METHOD THEREFOR

CROSS-REFERENCE TO RELATED APPLICATIONS

This application claims priority under 35 U.S.C § 119(a) to Japanese Patent Application No. 2021-122748 filed on 27 Jul. 2021. The above application is hereby expressly incorporated by reference, in its entirety, into the present application.

BACKGROUND OF THE INVENTION

1. Field of the Invention

The present invention relates to an endoscope system and an operation therefor capable of displaying a plurality of types of endoscopic images.

2. Description of the Related Art

In a medical field, diagnosis using an endoscope system including a light source device, an endoscope, and a processor device becomes widespread. In diagnosis using an endoscope system, an image (hereinafter, referred to as an endoscopic image) obtained by imaging an observation target that is a subject with an endoscope according to a method called image enhanced endoscopy (IEE) or image enhanced observation is used to emphasize and display a surface structure, a lesion, biological information, or the like of the observation target, and to obtain diagnostic support information for a doctor to diagnose the observation target.

For IEE, there is a method of generating each type of endoscopic image according to a method of performing digital image processing and using an endoscopic image obtained by imaging an observation target, a method of using an endoscopic image obtained by illuminating an observation target with specific illumination light, or the like. For example, a doctor selects a specific type of endoscopic image to determine biological information such as a region where blood vessels are densely packed or a region where oxygen saturation is low in an observation target, and emphasizes and displays these regions on a display or the like. Such display is useful as diagnostic support information for a doctor to diagnose an observation target.

There is an endoscope system in which, in a case of acquiring two types of image signals such as a first image pick-up signal and a second image pick-up signal, which are necessary for generating an oxygen saturation image, decreases in a luminance and a resolution of a normal observation image and a decrease in a frame rate thereof are suppressed such that a luminance and a resolution of an oxygen saturation image using the normal observation image and a decrease in a frame rate thereof are also suppressed by reducing a reading time of the second image pick-up signal more than a reading time of the image pick-up signal while providing a period in which illumination light is turned off (WO2015/136963A, corresponding to US2016/353972A1).

SUMMARY OF THE INVENTION

In a case where a plurality of types of endoscopic images are acquired by respectively applying a plurality of types of illumination light, assuming that a frame rate in imaging is the same as in a case of applying a single type of illumination light, a frame rate of capturing each type of endoscopic image is reduced. As in the case of WO2015/136963A, in a case where displaying is performed on the basis of one specific type of endoscopic image among captured endoscopic images, a reading time can be reduced by selecting and reading out pixels for the other endoscopic images, and a frame rate of the endoscopic image to be displayed can be increased. However, depending on details of desired IEE, it may be desired to display or analyze a plurality of types, for example, two or more types of endoscopic images while suppressing deterioration in image quality due to a decrease in a frame rate or reading of a selected pixel.

The present invention provides an endoscope system and an operation method therefor capable of displaying an endoscopic image of which deterioration in image quality is suppressed in a case where a plurality of types of endoscopic images are acquired.

According to an aspect of the present invention, there is provided an endoscope system including an endoscope that includes an image pick-up unit; a light source unit that irradiates a subject with each of a plurality of pieces of illumination light having different spectra; and a processor device that includes a processor, in which, in a first observation mode, the processor controls the light source unit such that the subject is irradiated with each of the plurality of pieces of illumination light in a preset order, controls the image pick-up unit such that the subject is imaged according to a preset first imaging frame rate during a first period in which first illumination light included in the plurality of the illumination light is applied, acquires a first image captured by the image pick-up unit during the first period, generates a first display image according to a first display frame rate higher than the first imaging frame rate on the basis of the first image, and performs control for displaying the first display image on a display.

The first display image preferably includes an image in which the first image is not changed.

It is preferable that, in the first observation mode, the processor controls the image pick-up unit such that the subject is imaged according to a preset second imaging frame rate during a second period in which second illumination light included in the plurality of the illumination light is applied, and acquires a second image captured by the image pick-up unit during the second period.

It is preferable that the processor performs control for displaying the second image on the display.

It is preferable that the processor controls the light source unit such that the subject is repeatedly irradiated with a pattern including each of the plurality of pieces of illumination light.

It is preferable that the processor controls the light source unit such that the subject is irradiated with the first illumination light or the second illumination light by repeating a pattern including the first illumination light and the second illumination light.

It is preferable that the processor controls the light source unit such that each of the plurality of pieces of illumination light is intermittently applied.

It is preferable that the processor controls the image pick-up unit such that, in a period of one frame including an image pick-up period in which the image pick-up unit performs image pick-up and a reading period in which an image signal obtained through the image pick-up is read, the image pick-up period is longer than the reading period.

It is preferable that the processor controls the light source unit such that any of the plurality of pieces of illumination light is turned off and applied at least once during the image pick-up period.

It is preferable that the processor controls the light source unit such that an irradiation period in which any of the plurality of pieces of illumination light is applied is changed and the illumination light is applied.

It is preferable that the processor controls the image pick-up unit such that an exposure period is changed on the basis of the changed irradiation period.

It is preferable that the processor controls a light emission amount of the illumination light applied by the light source unit in one irradiation.

It is preferable that the light emission amount is calculated on the basis of an irradiation period in which the light source unit applies the illumination light and an instantaneous light emission amount that is a light emission amount in a unit time of the illumination light.

It is preferable that, in a second observation mode that is switchable from the first observation mode, the processor controls the light source unit such that the subject is irradiated with third illumination light included in the plurality of pieces of illumination light, controls the image pick-up unit such that the subject is imaged according to a preset third imaging frame rate during a third period in which the third illumination light is applied, acquires a third image captured by the image pick-up unit during the third period, and in a case where the third image is displayed on the display, generates a third display image according to a third display frame rate that is equal to or lower than a third imaging frame rate.

According to another aspect of the present invention, there is provided an operation method for an endoscope system including an endoscope that includes an image pick-up unit, a light source unit that irradiates a subject with each of a plurality of pieces of illumination light having different spectra; and a processor device that includes a processor, the operation method including causing the processor in a first observation mode to execute a step of controlling the light source unit such that the subject is irradiated with each of the plurality of pieces of illumination light in a preset order; a step of controlling the image pick-up unit such that the subject is imaged according to a preset first imaging frame rate during a first period in which first illumination light included in the plurality of the illumination light is applied; a step of acquiring a first image captured by the image pick-up unit during the first period; a step of generating a first display image according to a first display frame rate higher than the first imaging frame rate on the basis of the first image; and a step of performing control for displaying the first display image on a display.

According to the present invention, in a case where a plurality of types of endoscopic images are acquired, it is possible to display an endoscopic image of which deterioration in image quality is suppressed.

DESCRIPTION OF THE PREFERRED EMBODIMENTS

Figure 1:
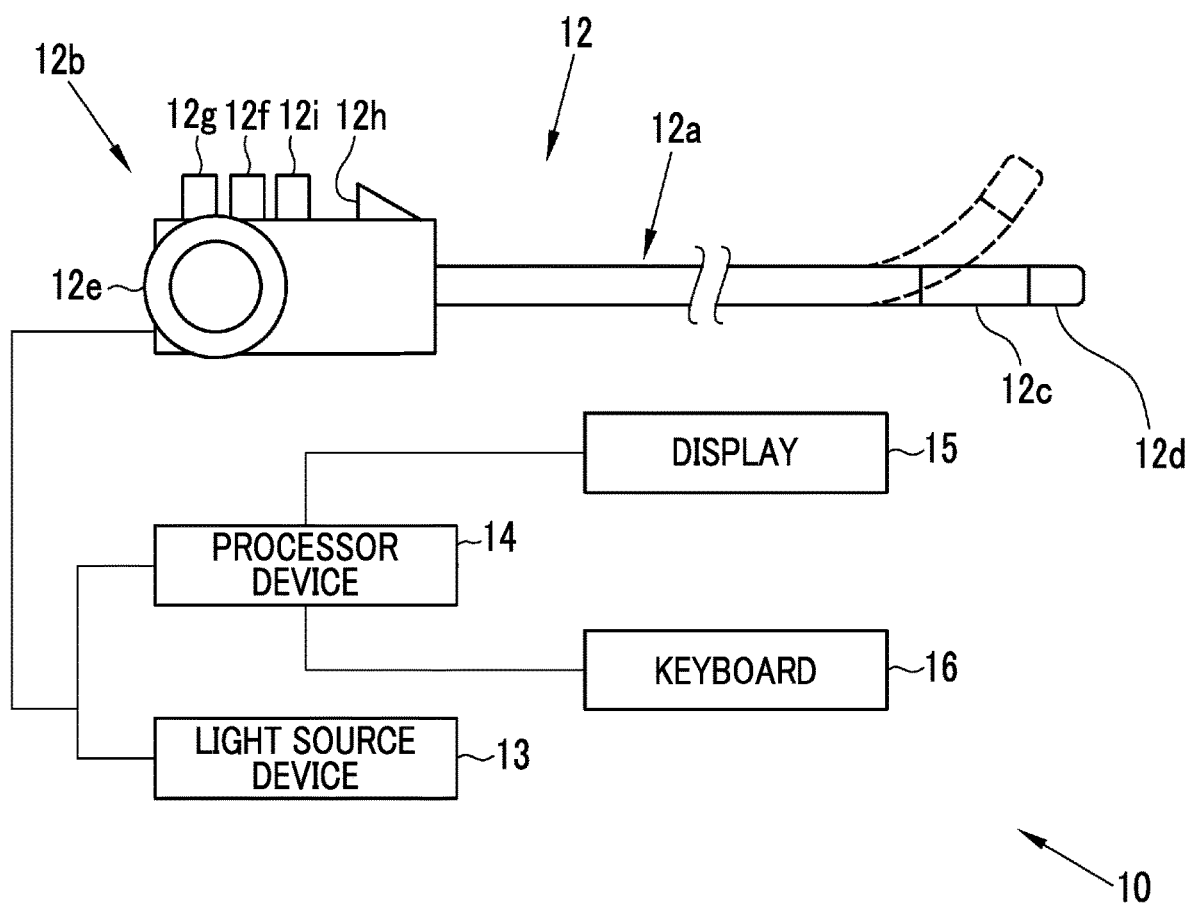
FIG. 1 is a schematic diagram of an endoscope system.

As shown in FIG. 1, an endoscope system 10 includes an endoscope 12, a light source device 13, a processor device 14, a display 15, and a keyboard 16. The endoscope 12 is optically connected to the light source device 13 and electrically connected to the processor device 14. The various connections are not limited to wired connections, and may be wireless connections, or may be connections using a network.

The endoscope 12 is provided on an insertion part 12a to be inserted into the body of a subject having an observation target, an operating part 12b provided at a base end portion of the insertion part 12a, and a bendable part 12c and a tip part 12d provided at a distal end side of the insertion part 12a. The bendable part 12c is bent by operating an angle knob 12e of the operating part 12b. The tip part 12d includes an image pick-up sensor 45 that is an image pick-up unit, and is directed in a desired direction through a bending operation of the bendable part 12c. A forceps channel (not shown) for inserting a treatment tool or the like is provided from the insertion part 12a to the tip part 12d. The treatment tool is inserted into the forceps channel from a forceps port 12h. Air supply, water supply, or suction is also performed from the forceps port 12h.

The operating part 12b includes a zoom operating part 12f for changing an image pick-up magnification, a mode selector switch 12g used for an observation mode switching operation, and a freeze switch 12i for acquiring a still image, in addition to the angle knob 12e. An observation mode switching operation, a zoom operation, or a still image acquisition operation may be an operation or an instruction using a keyboard 16 or a foot switch (not shown) in addition to the mode selector switch 12g, the zoom operating part 12f, or the freeze switch.

The endoscope system 10 includes a first observation mode and a second observation mode. In the first observation mode, a plurality of types of endoscopic images are acquired, and one or more types of endoscopic images are displayed on the display 15. The second observation mode is an observation mode in which one type of endoscopic image is acquired, and the acquired one type of endoscopic image is displayed on the display 15.

The type of endoscopic image is distinguished by the type of illumination light and/or details of image processing. The type of illumination light is distinguished by a spectrum (spectral characteristics) of the illumination light. Therefore, in a case where spectra of pieces of illumination light at the time of imaging are different from each other, captured endoscopic images are of different types.

In the present embodiment, in the first observation mode, a first image obtained by imaging an observation target by using first illumination light and a second image obtained by imaging an observation target by using second illumination light are acquired. In the second observation mode, a third image obtained by imaging an observation target by using third illumination light is acquired.

In the first observation mode, two types of images such as a normal image (first image) that is an endoscopic image having a natural hue obtained by imaging an observation target by using white light as the first illumination light and a special image (second image) obtained by imaging an observation by emitting special light (second illumination light) that is illumination light having a specific spectrum different from that of the white light, and the two types of images are arranged and displayed on the display 15. In the second observation mode, a normal image (third image) using white light as third illumination light is acquired, and the normal image (third image) is displayed on the display 15. The first illumination light and the third illumination light, or the second illumination light and the third illumination light may be the same or different. In the present embodiment, the first illumination light and the third illumination light are the same white light.

In the present embodiment, the second image is a color difference expansion processed image obtained by performing a color difference expansion process on a special image that is obtained by emitting the second illumination light and imaging an observation target. As the second image, a special image obtained by emitting special light that is illumination light having a specific spectrum different from that of white light and imaging an observation target without performing a color difference expansion process on an endoscopic image or a pseudo-color processed image obtained by performing pseudo-color processing may be used. The color difference expansion process or the pseudo-color processing will be described later.

The processor device 14 has a processor and is electrically connected to the display 15 and the keyboard 16. The display 15 displays an endoscopic image and/or various types of information acquired by the endoscope. The keyboard 16 functions as a user interface that receives input operations such as function settings. An external storage (not shown) for storing images, image information, or the like may be connected to the processor device 14.

Figure 2:
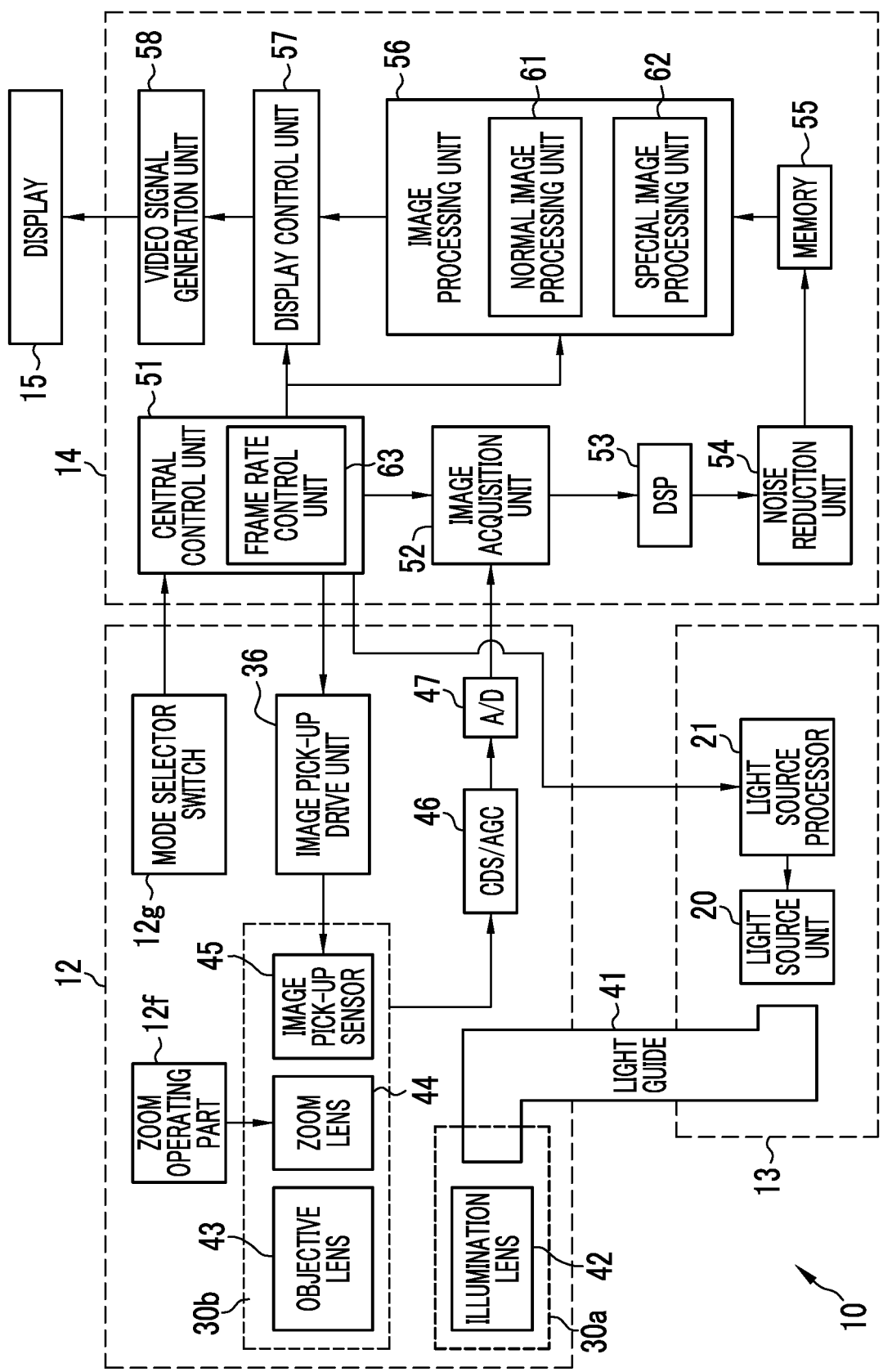
FIG. 2 is a block diagram showing a function of the endoscope system.

As shown in FIG. 2, the light source device 13 includes a light source unit 20 that emits illumination light to irradiate an observation target, and a light source processor 21 that controls the light source unit 20. The light source processor 21 is controlled by a central control unit 51 of the processor device 14.

The light source unit 20 is configured with, for example, a semiconductor light source such as multi-color light emitting diodes (LEDs), a combination of a laser diode and a phosphor, or a xenon lamp or a halogen light source. Each of a plurality of pieces of illumination light having different spectra is applied to the observation target. The light source unit 20 includes an optical filter or the like for adjusting a wavelength range of light emitted by the LED or the like. The light source processor 21 controls an amount of illumination light by turning on/off each LED or the like and adjusting a drive current or a drive voltage of each LED or the like. The light source processor 21 controls a wavelength range of the illumination light by changing an optical filter or the like.

Figure 3:
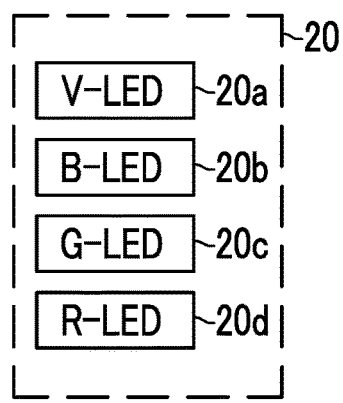
FIG. 3 is an explanatory diagram for describing four-color LEDs included in a light source unit.

As shown in FIG. 3, in the present embodiment, the light source unit 20 includes four color LEDs such as a violet light emitting diode (V-LED) 20a, a blue light emitting diode (B-LED) 20b, and a green light emitting diode (G-LED) 20c, and a red light emitting diode (R-LED) 20d.

Figure 4:
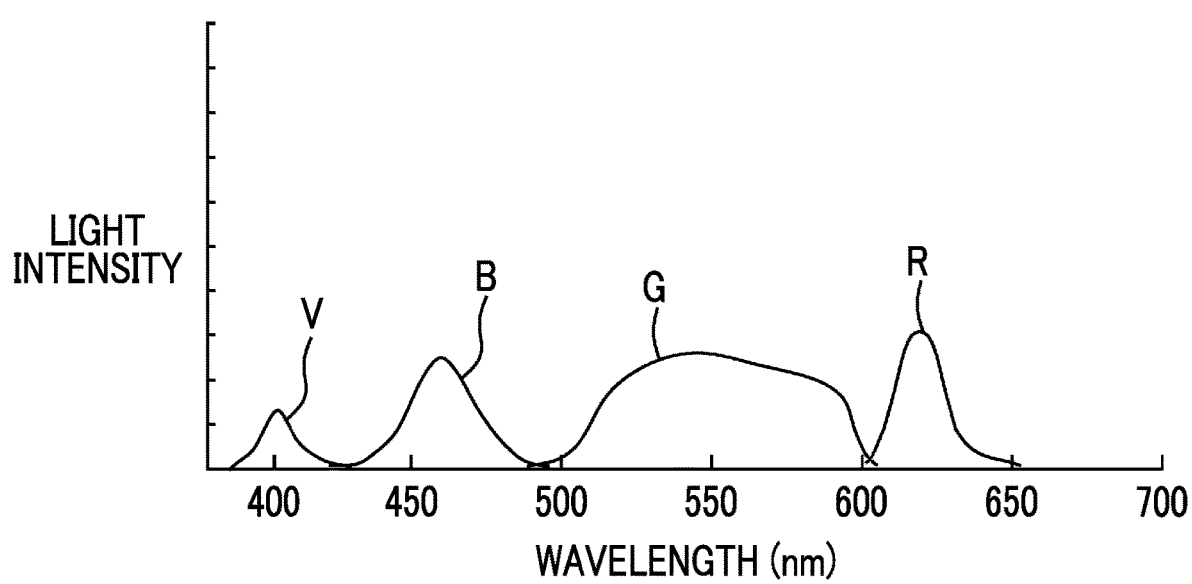
FIG. 4 is a graph showing spectra of violet light V, blue light B, green light G, and red light R.

As shown in FIG. 4, the V-LED 20a generates violet light V having a central wavelength of 410±10 nm and a wavelength range of 380 to 420 nm. The B-LED 20b generates blue light B having a central wavelength of 450±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm.

The light source processor 21 controls the V-LED 20a, the B-LED 20b, the G-LED 20c, and the R-LED 20d. In a case where the first observation mode is set, that is, during acquisition of a normal image, and the second observation mode is set, the light source processor 21 controls the respective LEDs 20a to 20d such that the first illumination light in which a combination of the light intensity ratios of the violet light V, the blue light B, the green light G, and the red light R is Vc:Bc:Gc:Rc is emitted. The first illumination light is white light.

Figure 5:
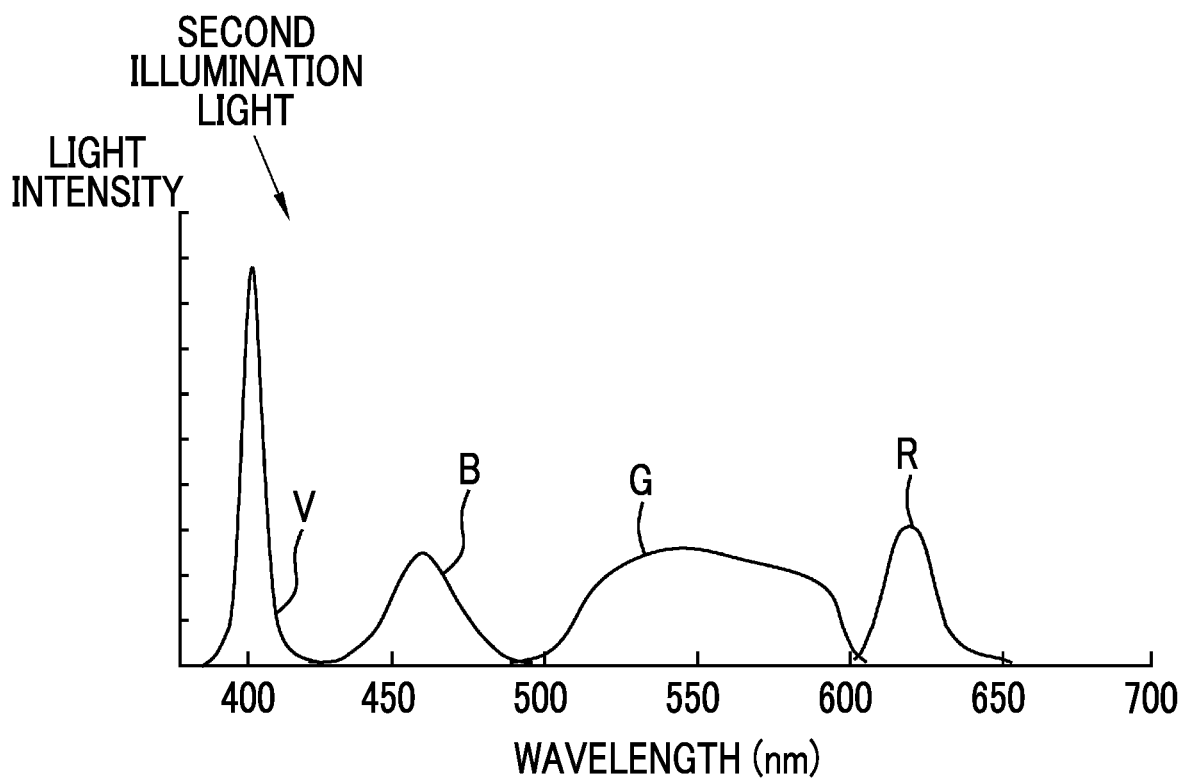
FIG. 5 is a graph showing a spectrum of second illumination light.

In a case where the first observation mode is set, that is, during acquisition of a special image, the processor 21 controls the respective LEDs 20a to 20d such that special light in which a combination of the light intensity ratios between the violet light V, the blue light B, the green light G, and the red light R is Vs:Bs:Gs:Rs is emitted. The special light is, for example, the second illumination light. It is preferable that the second illumination light is light with which an endoscopic image that emphasizes superficial blood vessel can be obtained. Thus, in the second illumination light, it is preferable that a light intensity of the blue light B is higher than a light intensity of the violet light V. For example, as shown in FIG. 5, a ratio between the light intensity Vsl of the violet light V and the light intensity Bsl of the blue light B is set to "4:1".

In the present specification, a combination of light intensity ratios includes a case where a ratio of at least one semiconductor light source is 0 (zero). Therefore, this includes a case where any one or more of the semiconductor light sources are not turned on. For example, as in a case where a combination of the light intensity ratios between the violet light V, the blue light B, the green light G, and the red light R is 1:0:0:0, even in a case where only one of the semiconductor light sources is turned on, and the other three are not turned on, a light intensity ratio is applied and is one of combinations of light intensity ratios.

As described above, combinations of the light intensity ratios of the violet light V, the blue light B, the green light G, and the red light R emitted as the first illumination light and the second illumination light, that is, the types of the illumination light are different from each other. Therefore, the first illumination light and the second illumination light have different spectra from each other. The light source processor 21 repeats a pattern formed of each of the plurality of pieces of illumination light, and controls each of the LEDs 20a to 20d such that an observation target is irradiated with each of the plurality of pieces of illumination light in a preset order.

In the present embodiment, in the first observation mode, different types of illumination light such as the first illumination light and the second illumination light are automatically switched and emitted, and in the second observation mode, the first illumination light is continuously emitted. In a case where the first illumination light and the second illumination light are automatically switched and emitted, for example, a first period in which the first illumination light is continuously emitted and a second period in which the second illumination light is continuously emitted are alternately repeated. More specifically, after the first period for emitting the first illumination light is performed with a preset number of frames, the second period for emitting the second illumination light is performed with a preset number of frames. Thereafter, the first period is reached again, and a pattern formed of the first period and the second period is repeated. Three or more types of illumination light may be switched and emitted. Also in this case, in the same manner as in the case of the two types of illumination light, illumination light is emitted in a preset order in a period corresponding to a preset number of frames in each type of illumination light, and this pattern is repeated. The pattern of the illumination light may be a pattern in which the same type of illumination light is used twice or more, and the illumination light used is not limited.

The "frame" means a unit for controlling an image pick-up sensor 45 (refer to FIG. 2) that images an observation target. For example, "1 frame" means a period including at least an image pick-up period in which the image pick-up sensor 45 is exposed to capture an image with light from the observation target and a reading period in which an image signal is read. One captured endoscopic image corresponds to one frame. In the present embodiment, various periods such as a first period, a second period, and a third period are defined to correspond to a "frame" that is the unit of imaging. The various periods such as the first, second, and third periods may have the same number of frames as that of each period, or may have different numbers of frames, and can be set without limitation.

Figure 6:
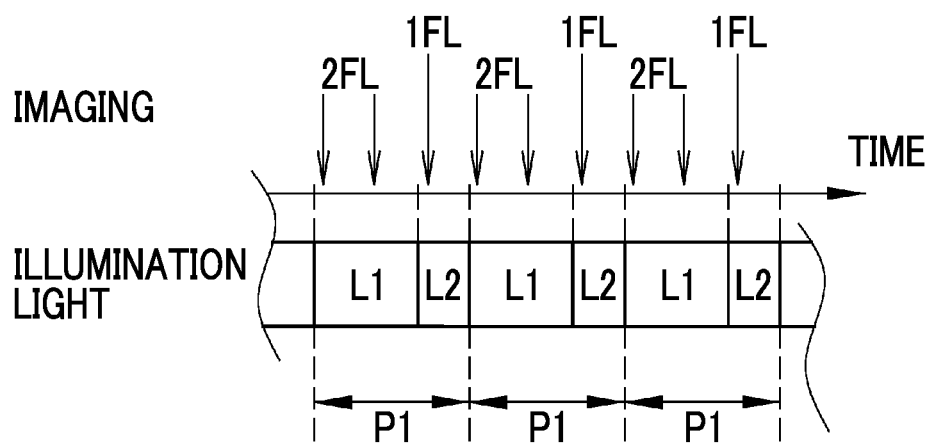
FIG. 6 is an explanatory diagram for describing an example of a pattern of illumination light and imaging.

As shown in FIG. 6, in the present embodiment, first illumination light L1 is applied with two frames (2FL) as the first period, and then second illumination light L2 is applied with one frame (1FL) as the second period. A combination of the first illumination light L1 and the second illumination light L2 is set as a pattern P1, and the pattern P1 is repeated.

The light emitted by each of the LEDs 20a to 20e is incident to a light guide 41 via an optical path coupling portion (not shown) configured with a mirror, a lens, and the like. The light guide 41 is built in the endoscope 12 and a universal cord (a cord connecting the endoscope 12, the light source device 13, and the processor device 14 to each other).

The light guide 41 propagates light from the optical path coupling portion to the tip part 12d of the endoscope 12.

An illumination optical system 30a and an image pick-up optical system 30b are provided at the tip part 12d of the endoscope 12. The illumination optical system 30a has an illumination lens 42, and the illumination light propagated by the light guide 41 is applied to the observation target via the illumination lens 42. The image pick-up optical system 30b has an image pick-up drive unit 36, an objective lens 43, a zoom lens 44, and an image pick-up sensor 45. Various types of light such as reflected light, scattered light, and fluorescence from the observation target are incident to the image pick-up sensor 45 via the objective lens 43 and the zoom lens 44. Consequently, an image of the observation target is formed on the image pick-up sensor 45. The zoom lens 44 freely moves between the telephoto end and the wide end by operating the zoom operating part 12f, and enlarges or reduces the image of the observation target formed on the image pick-up sensor 45.

Figure 7:
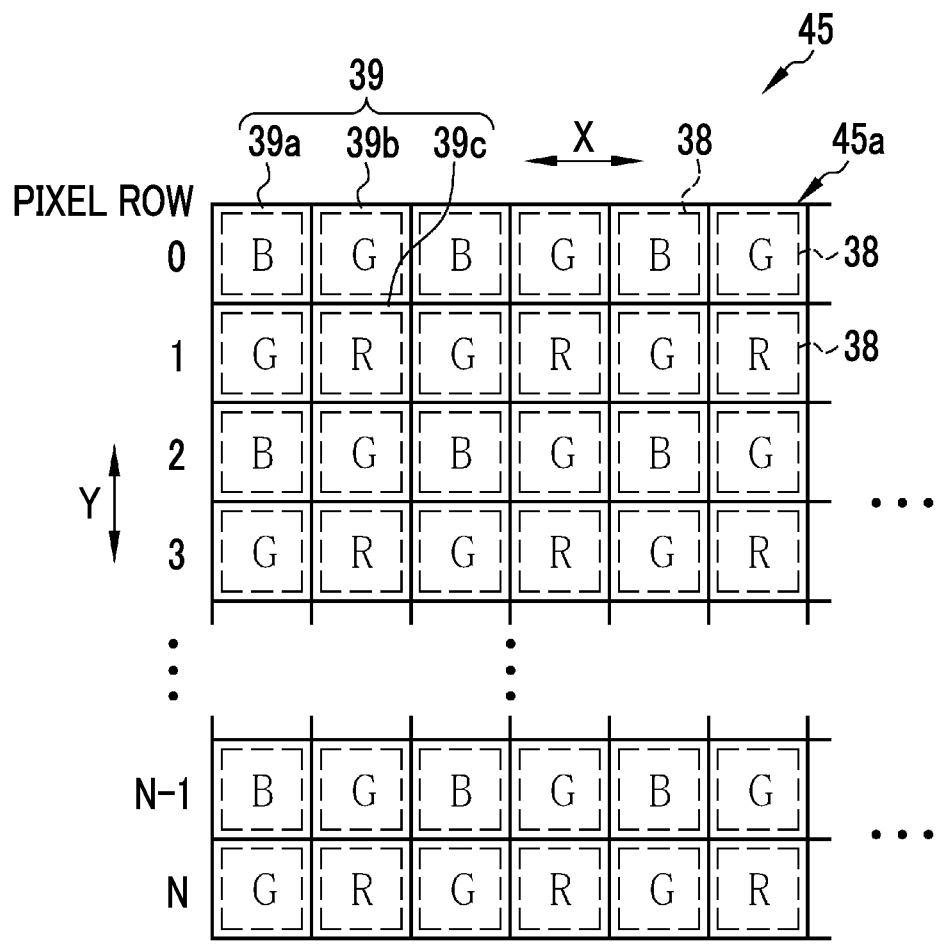
FIG. 7 is an explanatory diagram showing a configuration of an image pick-up sensor.

The image pick-up sensor 45 is a color image pick-up element, and captures an optical image of an observation target and outputs an image signal. In the present embodiment, a complementary metal oxide semiconductor (CMOS) image sensor is used. As shown in FIG. 7, a plurality of pixels 38 that generate pixel signals through photoelectric conversion are formed on an image pick-up surface 45a of the image pick-up sensor 45. The pixels 38 are two-dimensionally arranged in a matrix in a row direction (X direction) and a column direction (Y direction).

A color filter array 39 is provided on a light incident side of the image pick-up sensor 45. The color filter array 39 has a blue (B) filter 39a, a green (G) filter 39b, and a red (R) filter 39c. One of these filters is located on each pixel 38. A color array of the color filter array 39 is a Bayer array, in which the G filter 39b is arranged in a checkered pattern every other pixel, and the B filter 39a and the R filter 39c are arranged in a square grid on the remaining pixels.

Hereinafter, the pixel 38 on which the B filter 39a is disposed will be referred to as a B pixel, the pixel 38 on which the G filter 39b is disposed will be referred to as a G pixel, and the pixel 38 on which the R filter 39c is disposed will be referred to as an R pixel. The B pixels and the G pixels are alternately arranged in each of even-numbered (0, 2, 4, . . . , and N−1) pixel rows. The G pixels and the R pixels are alternately arranged in each of odd-numbered (1, 3, 5, . . . , and N) pixel rows. Here, N is a positive integer, and the pixel row refers to the pixels 38 for one row arranged in the row direction. The pixel row refers to pixels 38 for one row arranged in the column direction.

Figure 8:
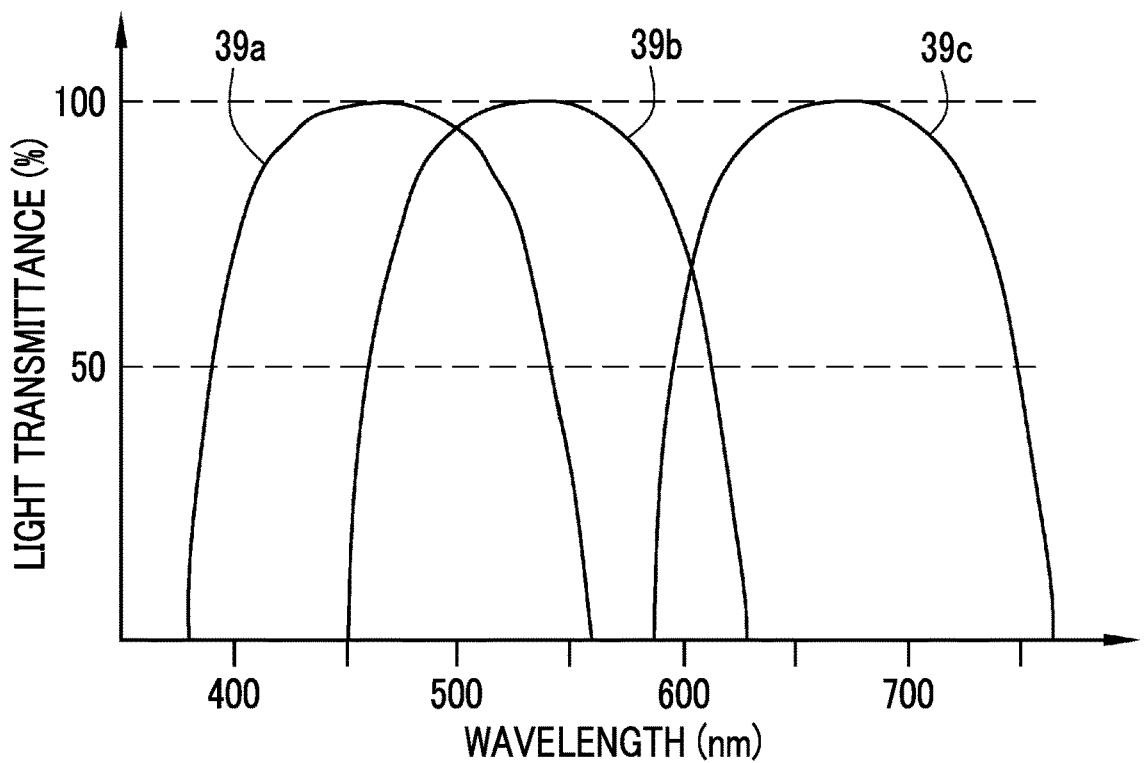
FIG. 8 is a graph showing the light transmittance of a color filter.

The color filter array 39 has spectral characteristics shown in FIG. 8. The B filter 39a has a high light transmittance for a wavelength range of, for example, 380 nm to 560 nm. The G filter 39b has a high light transmittance for a wavelength range of, for example, 450 nm to 630 nm. The R filter 39c has a high light transmittance for a wavelength range of, for example, 580 nm to 760 nm.

The image pick-up sensor 45 is driven by the image pick-up drive unit 36, receives return light from an observation target illuminated by the illumination light with the plurality of pixels 38 via the color filter array 39, and outputs image signals. The image pick-up sensor 45 outputs BGR image signals including a B pixel signal, a G pixel signal, and an R pixel signal as image signals.

In the present embodiment, a CMOS image sensor is used as the image pick-up sensor 45, but the CMOS image sensor generally performs an image pick-up operation according to a rolling shutter method. In the rolling shutter method, the image pick-up sensor 45 executes signal reading according to a "sequential reading method". In the sequential reading method, signal reading is sequentially performed by one pixel row from the first pixel row "0" to the last pixel row "N" for all pixels 38.

The image pick-up sensor 45 can execute a "sequential reset method" and a "batch reset method" as a reset method. In the sequential reset method, resetting is sequentially performed by one pixel row from the first pixel row "0" to the last pixel row "N". In the batch reset method, all pixel rows are reset at a time at the same time. In the present embodiment, resetting is performed according to a sequential reset method.

In the present embodiment, the rolling shutter type CMOS image sensor is used as the image pick-up sensor 45, but the present invention is not limited to this, and a global shutter type CMOS image sensor may be used. As the image pick-up sensor 45, a charge coupled device (CCD) image sensor may be used instead of the CMOS image sensor.

Instead of the image pick-up sensor 45 provided with the primary color filters, a complementary image pick-up sensor provided with cyan (C), magenta (M), yellow (Y), and G (green) complementary filters may be used. In a case where a complementary image pick-up sensor is used, image signals of four colors of CMYG are output. Therefore, the same RGB image signals as in the image pick-up sensor 45 can be obtained by converting image signals of the four colors of CMYG into image signals of the three colors of RGB through complementary-primary color conversion. Instead of the image pick-up sensor 45, a monochrome sensor without a color filter may be used.

The image pick-up sensor 45 is driven and controlled by the central control unit 51 (refer to FIG. 2) via the image pick-up drive unit 36. The central control unit 51 controls light emission of the light source unit 20 via the light source processor 21 in synchronization with the drive of the image pick-up sensor 45. By controlling the image pick-up sensor 45 such that an observation target illuminated by the first illumination light L1 that is white light is imaged, a Bc image signal is output from the B pixel of the image pick-up sensor 45, a Gc image signal is output from the G pixel, and an Rc image signal is output from the R pixel. Similarly, by controlling the image pick-up sensor 45 such that an observation target illuminated by the second illumination light L2 that is special light is imaged, a Bs image signal is output from the B pixel of the image pick-up sensor 45, a Gs image signal is output from the G pixel, and an Rs image signal is output from the R pixel.

The central control unit 51 includes a frame rate control unit 63 (refer to FIG. 2). The frame rate indicates the number of frames per unit time, and the unit is fps (frames per second). The frame rate control unit 63 controls a frame rate such as an imaging frame rate in a case of capturing an endoscopic image or a display frame rate in a case of displaying an endoscopic image. The frame rate control unit 63 will be described later.

A correlated double sampling/automatic gain control (CDS/AGC) circuit 46 performs correlated double sampling (CDS) or automatic gain control (AGC) on an analog image signal obtained from the image pick-up sensor 45. The image signal that has passed through the CDS/AGC circuit 46 is converted into a digital image signal by an analog/digital (A/D) converter 47. The digital image signal after A/D conversion is input to the processor device 14.

In the processor device 14, a program related to image pick-up control or processes such as image processing is stored in a program memory (not shown). In the processor device 14, the program in the program memory is operated by the central control unit 51 configured with an image processor or the like that is a first processor, to realize functions of a central control unit 51, an image acquisition unit 52, a digital signal processor (DSP) 53, a noise reduction unit 54, a memory 55, an image processing unit 56, a display control unit 57, and a video signal generation unit 58. The central control unit 51 receives information from the endoscope 12 and the light source device 13, and controls each unit of the processor device 14 and also controls the endoscope 12 or the light source device 13 on the basis of the received information. The central control unit 51 also receives information such as instructions from the keyboard 16.

Figure 9:
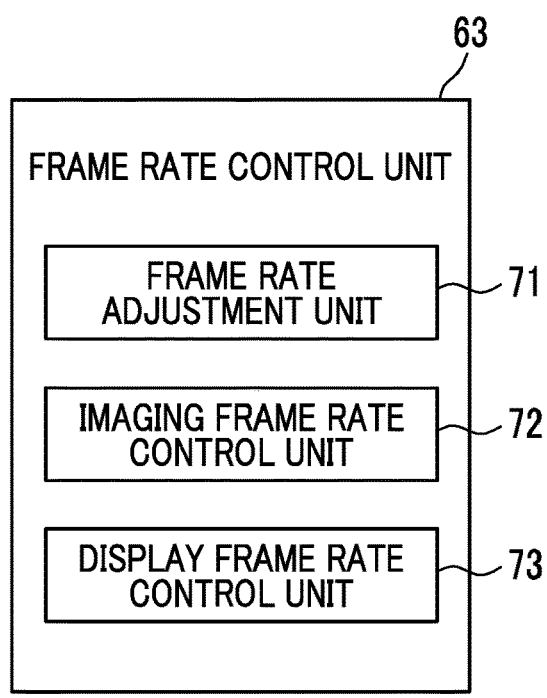
FIG. 9 is a block diagram showing a function of a frame rate control unit.

As shown in FIG. 9, the frame rate control unit 63 included in the central control unit 51 includes a frame rate adjustment unit 71, an imaging frame rate control unit 72, and a display frame rate control unit 73.

The frame rate adjustment unit 71 adjusts the imaging frame rate and the display frame rate to satisfy preset conditions. Conditions regarding the imaging frame rate and the display frame rate are set according to the type of endoscopic image to be acquired. Therefore, the conditions regarding the imaging frame rate and the display frame rate are set according to the type of illumination light in a case of acquiring an endoscopic image.

In the first observation mode, the frame rate adjustment unit 71 sends an instruction to the imaging frame rate control unit 72 such that an observation target is imaged according to a first imaging frame rate in the first period of applying the first illumination light L1, and sends an instruction to the display frame rate control unit 73 in a case where an obtained first image is displayed on the display 15 such that the first image is displayed according to a first display frame rate.

In the first observation mode, the frame rate adjustment unit 71 sends an instruction to the imaging frame rate control unit 72 such that an observation target is imaged according to a second imaging frame rate in the second period of applying the second illumination light L2, and sends an instruction to the display frame rate control unit 73 in a case where an obtained second image is displayed on the display 15 such that the second image is displayed according to a second display frame rate.

The frame rate adjustment unit 71 is preset with a condition that the first display frame rate is higher than the first imaging frame rate as a condition regarding the first image to be acquired. Therefore, the frame rate adjustment unit 71 sends an instruction to each of the imaging frame rate control unit 72 and the display frame rate control unit 73 according to the preset first imaging frame rate and the first display frame rate higher than the first imaging frame rate.

As a condition regarding the second image to be acquired, a condition that the second imaging frame rate and the second display frame rate are the same is set in advance. Therefore, the frame rate adjustment unit 71 sends an instruction to each of the imaging frame rate control unit 72 and the display frame rate control unit 73 according to the same second display frame rate as the preset second imaging frame rate.

The imaging frame rate control unit 72 adjusts an imaging frame rate on the basis of the instruction regarding the first imaging frame rate sent from the frame rate adjustment unit 71. In the first observation mode, the imaging frame rate control unit 72 controls the image pick-up sensor 45 and the like such that the observation target is imaged according to the first imaging frame rate in the first period of applying the first illumination light L1. An operation of the display frame rate control unit 73 will be described later.

The image acquisition unit 52 acquires a digital image signal for an endoscopic image input from the endoscope 12. The image acquisition unit 52 acquires an image signal obtained by imaging an observation target illuminated by each type of illumination light for each frame.

The acquired image signal is transmitted to the DSP 53. The DSP 53 performs digital signal processing such as a color correction process on the received image signal. The noise reduction unit 54 performs a noise reduction process on the basis of, for example, a moving average method, or a median filter method on the image signal subjected to the color correction process or the like by the DSP 53. The image signal with reduced noise is stored in the memory 55.

The image processing unit 56 acquires an image signal after noise reduction from the memory 55. The acquired image signal is subjected to signal processing such as a color conversion process, a color enhancement process, and a structure enhancement process as necessary to generate a color endoscopic image in which the observation target is captured. The image processing unit 56 includes a normal image processing unit 61 and a special image processing unit 62.

The normal image processing unit 61 performs image processing for a normal image such as a color conversion process, a color enhancement process, and a structure enhancement process on an input image signal for the normal image after noise reduction for one frame in the first observation mode or the second observation mode. The image signal subjected to the image processing for a normal image is input as a normal image to the display control unit 57.

In the first observation mode, the special image processing unit 62 performs image processing for a special image such as a color conversion process, a color enhancement process, and a structure enhancement process on an input image signal for the special image after noise reduction for one frame. The image signal subjected to the image processing for the special image is input as a special image to the display control unit 57.

The endoscopic image generated by the image processing unit 56 is a normal image or a special image, and details of the color conversion process, the color enhancement process, and the structure enhancement process differ depending on the type of the endoscopic image. In the case of the normal image, the image processing unit 56 generates the normal image by performing the various types of signal processing described above such that the observation target has a natural hue. In the case of the special image, the image processing unit 56 generates the special image by, for example, performing the various types of signal processing for emphasizing a blood vessel of the observation target.

Here, a description will be made of a color difference expansion process in a case where the second image is a color difference expansion processed image obtained by performing a color difference expansion process on an endoscopic image that is obtained by emitting the second illumination light L2 and imaging an observation target. In the color difference expansion process, first, a first signal ratio (Bs/Gs) representing a ratio between the Bs image signal and the Gs image signal and a second signal ratio (Gs/Rs) representing a ratio between the Rs image signal and the Gs image signal are calculated. A color difference expansion process for expanding a color difference between a plurality of observation target ranges is performed on the basis of the first signal ratio and the second signal ratio, and a color difference expanded image is generated on the basis of the first signal ratio and the second signal ratio after the color difference expansion process. The color difference expansion process is a kind of color enhancement process. The color difference expanded image is the second image.

Figure 10:
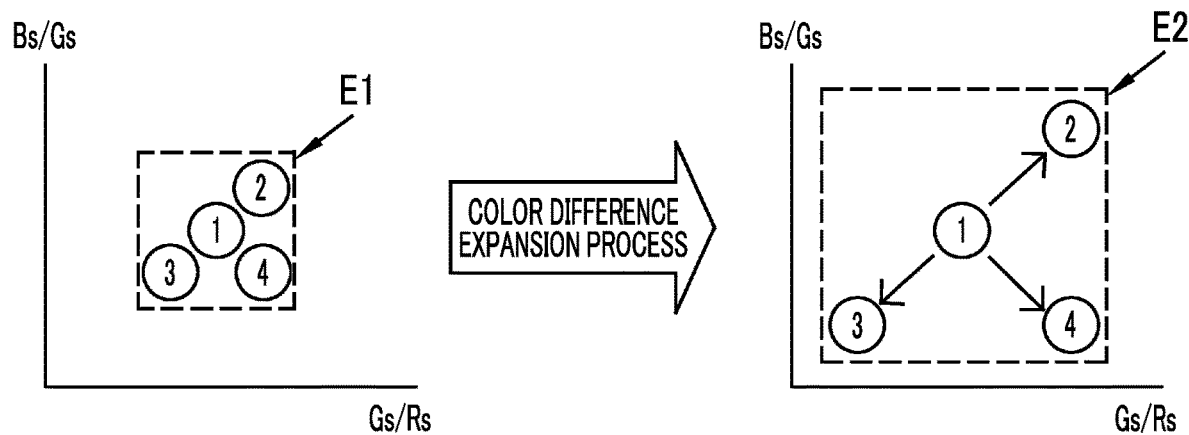
FIG. 10 is an explanatory diagram for describing a color difference expansion process.

Regarding the color difference expansion process, as shown in FIG. 10, it is preferable that a distance between a plurality of observation target ranges is expanded in a two-dimensional space formed by the first signal ratio (Bs/Gs) and the second signal ratio (Gs/Rs). Specifically, it is preferable that, in a two-dimensional space, in a state in which a position of a first range (indicated by 1 surrounded by a circle) among a plurality of observation target ranges is maintained before and after the color difference expansion process, a distance between the first range and a second range (indicated by 2 surrounded by a circle), a distance between the first range and a third range (indicated by 3 surrounded by a circle), and a distance between the first range and a fourth range (indicated by 4 surrounded by a circle) are expanded. It is preferable that the color difference expansion process is performed according to a method of adjusting a radius and an angle after converting the first signal ratio and the second signal ratio into polar coordinates. It is preferable that the first range is a normal part in which no lesion or the like is present, and the second to fourth ranges are abnormal parts in which a lesion or the like may be present. Through the color difference expansion process, a range E1 in the two-dimensional space before the color difference expansion process is expanded to a range E2 after the color difference expansion process, and thus an image in which a color difference is emphasized, for example, a color difference between an abnormal part and a normal part is emphasized is obtained. It is preferable to use this image as the second image.

A description will be made of pseudo-color processing in a case where the second image is a pseudo-color processed image obtained by performing pseudo-color processing on an endoscopic image obtained by emitting the second illumination light L2 and imaging an observation target. The pseudo-color processing is a process of allocating the Bs image signal to a B channel and a G channel for display and allocating the Gs image signal to an R channel for display. Through this pseudo-color processing, an image in which a blood vessel or a structure having a specific depth such as a superficial blood vessel is emphasized can be obtained. This image may be used as the second image.

Figure 11:
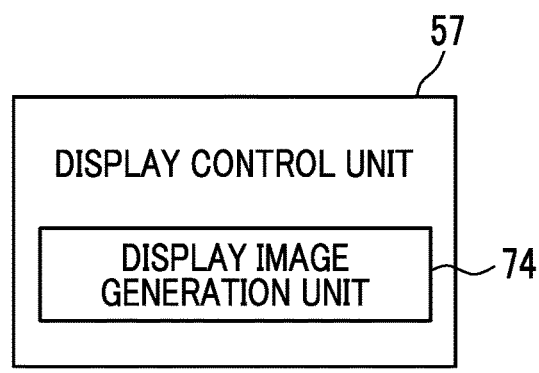
FIG. 11 is a block diagram showing a function of a display control unit.

The display control unit 57 receives the endoscopic image generated by the image processing unit 56 and performs control for displaying the endoscopic image on the display 15 under the control of the central control unit 51. As shown in FIG. 11, the display control unit 57 includes a display image generation unit 74. A display image is an image to be displayed on the display 15, and the display image generation unit 74 generates a display image from the endoscopic image generated by the image processing unit 56.

The display control unit 57 follows instructions from the frame rate adjustment unit 71 provided in the central control unit 51 for a frame rate in a case of displaying the display image. The display control unit 57 performs control for displaying the endoscopic image on the display 15 by generating a display image in response to an instruction from the frame rate adjustment unit 71.

An instruction from the frame rate adjustment unit 71 is given for each type of endoscopic image. Therefore, in a specific type of endoscopic image, for example, in a case where an instruction from the frame rate adjustment unit 71 is given for an imaging frame rate being different from a display frame rate, and is necessary, the display control unit 57 adjusts the number of display images generated by the display image generation unit 74, and thus controls an image to be displayed on the display 15 in response to the instruction from the frame rate adjustment unit 71.

Specifically, there may be the following three cases as instructions for a specific type of endoscopic image from the frame rate adjustment unit 71. First, in an instruction from the frame rate adjustment unit 71, a display frame rate is the same as an imaging frame rate. In this case, the display image generation unit 74 generates a captured endoscopic image as a display image without any processing. Second, in an instruction from the frame rate adjustment unit 71, a display frame rate is lower than an imaging frame rate. In this case, the display image generation unit 74 generates an endoscopic image selected from endoscopic images obtained through imaging as a display image to match the display frame rate. Third, in an instruction from the frame rate adjustment unit 71, a display frame rate is higher than an imaging frame rate. In this case, the display image generation unit 74 generates a captured endoscopic image as a display image without any processing, generates a new display image on the basis of the captured endoscopic image, and uses the new display image as a display image.

In the present embodiment, the frame rate adjustment unit 71 sends, to the display control unit 57, a condition that a display frame rate is higher than an imaging frame rate for the first image. A condition that the second image is captured but is not displayed, that is, an imaging frame rate is a specific imaging frame rate higher than 0 fps and a display frame rate is 0 fps is sent to the display control unit 57. In this case, the display image generation unit 74 performs frame interpolation on the basis of, for example, the past first image captured in order to generate the new first display image on the basis of the captured first image.

In the frame interpolation, an endoscopic image generated on the basis of a past endoscopic image captured is used as an interpolation frame. A method of generating an interpolation frame may be selected depending on cases. For example, an interpolation frame may be generated according to an addition averaging method, a movement vector method, a duplication method, or the like by using a captured endoscopic image. By using the interpolation frame in combination with the frame of the originally captured endoscopic image, the number of frames of the endoscopic image to be displayed is increased, and the condition that the display frame rate is higher than the capture frame rate can be satisfied.

In the method of generating an interpolation frame according to the addition averaging method, for example, in a case where a new image generated by using a plurality of past endoscopic images captured may be used as a display image, an average value of image signal values may be calculated for respective endoscopic images used, a display image may be generated on the basis of a value obtained by adding and averaging the number of endoscopic images using this average values, and this display image may be used as an interpolation frame. The addition average means a simple average obtained through simple averaging, but in some cases, a weighted average obtained through weighting and then averaging may be used for any of the endoscopic images depending on cases. A weighting factor may be preset. The present invention is not limited to using two endoscopic images, and a display image may be generated by performing addition averaging by using three or more endoscopic images.

In the present embodiment, in the instruction from the frame rate adjustment unit 71, regarding the first image, a first imaging frame rate that is an imaging frame rate of the first image is set to 30 fps, and a first display frame rate that is a display frame rate of the first image is set to 60 fps. In an instruction from the frame rate adjustment unit 71, regarding the second image, a second imaging frame rate that is an imaging frame rate of the second image is set to 15 fps, and a second display frame rate that is a second display frame rate of the second image is set to 0. The pattern P1 in which the first illumination light L1 and the second illumination light L2 are respectively applied for two frames and one frame (FIG. 6) is repeated, and an imaging frame rate and a display frame rate of the first image and the second image are also repeated by the frame rates with the values in the above instruction.

Figure 12:
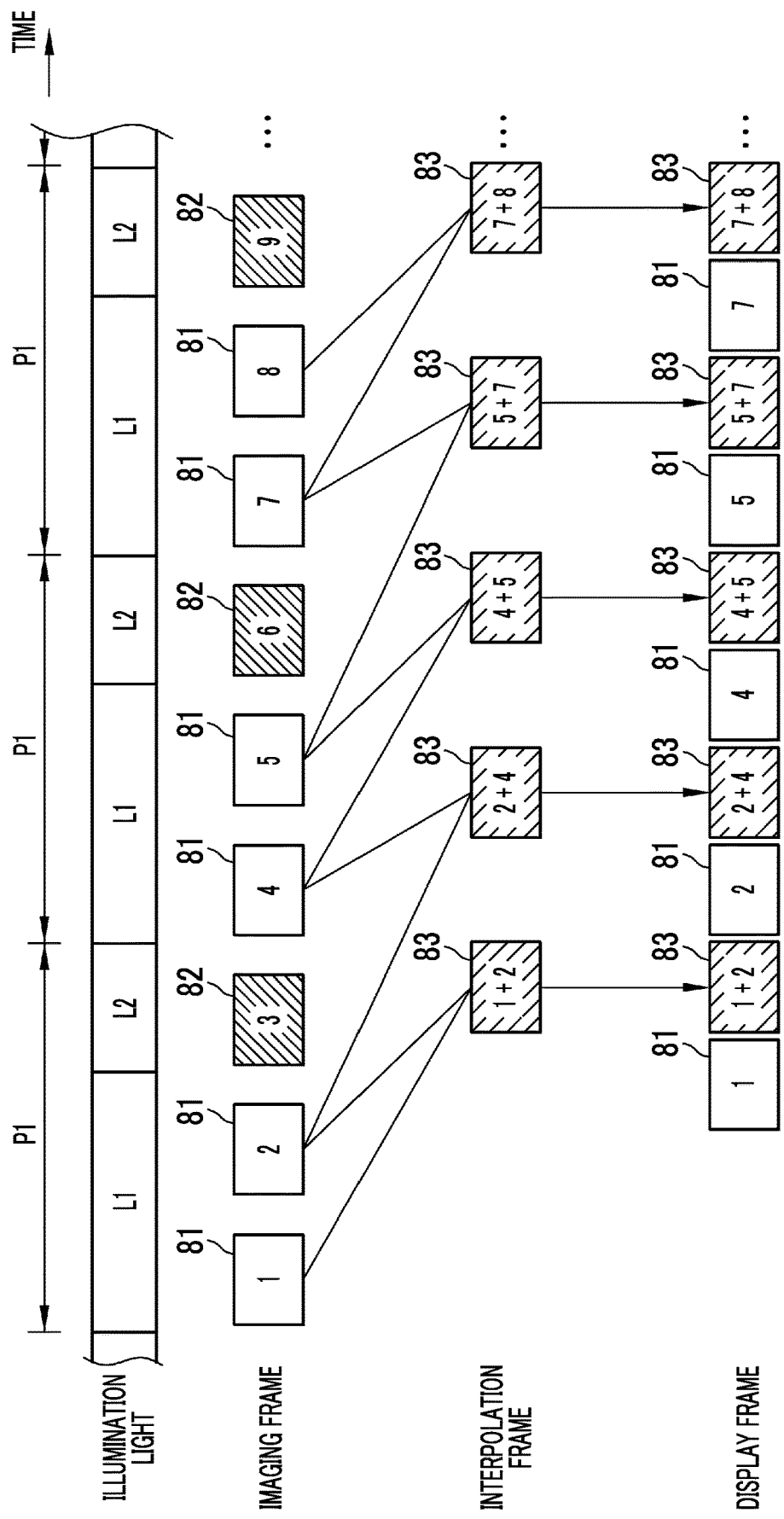
FIG. 12 is an explanatory diagram for describing an imaging frame, an interpolation frame, and a display frame.

As shown in FIG. 12, regarding an imaging frame, a first image 81 is captured for two frames with the first illumination light L1 in the first period, and then a second image 82 is captured for one frame with the second illumination light L2 in the subsequent second period. The pattern P1 of this combination is repeated. The numbers assigned to the first image 81, an interpolation frame 83, and the second image 82 written in the columns of the imaging frame, the interpolation frame, and the display frame are numbers 1 to 9 in the order of the imaging time. The second image 82 is shaded. The interpolation frame is shaded differently from the second image 82.

As shown in the column of the imaging frame in FIG. 12, the frame rate adjustment unit 71 sets a condition in which an imaging frame rate is 30 fps and a display frame rate is 60 fps for the first image 81, and an imaging frame rate is 15 fps and a display frame rate is 0 fps for the second image 82. Therefore, as shown in the column of the interpolation frame, the display image generation unit 74 generates a new display image as the interpolation frame 83 at a rate of 30 fps on the basis of the captured first image 81. As shown in the column of the display frame, the captured first image 81 and the interpolation frame 83 are combined to generate frames at 60 fps, and the frames are displayed on the display 15. As described above, all the display frames are images based on the first image 81. Therefore, the first display image includes an image in which the first image 81 is not changed and the interpolation frame 83 in which the first image 81 is changed.

In the present embodiment, the interpolation frame 83 is generated according to the addition averaging method. The interpolation frame 83 marked with "1+2" indicates an interpolation frame 83 generated by adding and averaging two first images 81 such as the first image 81 of No. 1 and the first image 81 of No. 2. The first image 81 of No. 1 and the first image 81 of No. 2 take addition averaging of image signals at a ratio of 50:50, but a ratio is not limited to this. In a case of displaying the interpolation frame 83, as a display frame, the interpolation frame 83 is disposed between the first image 81 and the first image 81 used for generating the interpolation frames 83 in a time series. In the movement vector method, the duplication method, or the like, the interpolation frame 83 may be disposed and displayed in the same manner. As described above, according to the first display frame rate higher than the first imaging frame rate, the first display image that is a display image of the first image 81 can be generated, and the condition for the first imaging frame rate and the first display frame rate can be satisfied.

In the method of generating an interpolation frame according to the movement vector method, for example, in a case where a new image generated by using a plurality of past endoscopic images captured is used as a display image, an average value of image signal values may be calculated for respective endoscopic images used, a movement vector calculated on the basis of each of these endoscopic images may be referred to, a display image may be generated on the basis of a value obtained through weighted averaging of the endoscopic images used, and this display image may be used as an interpolation frame.

Figure 13:
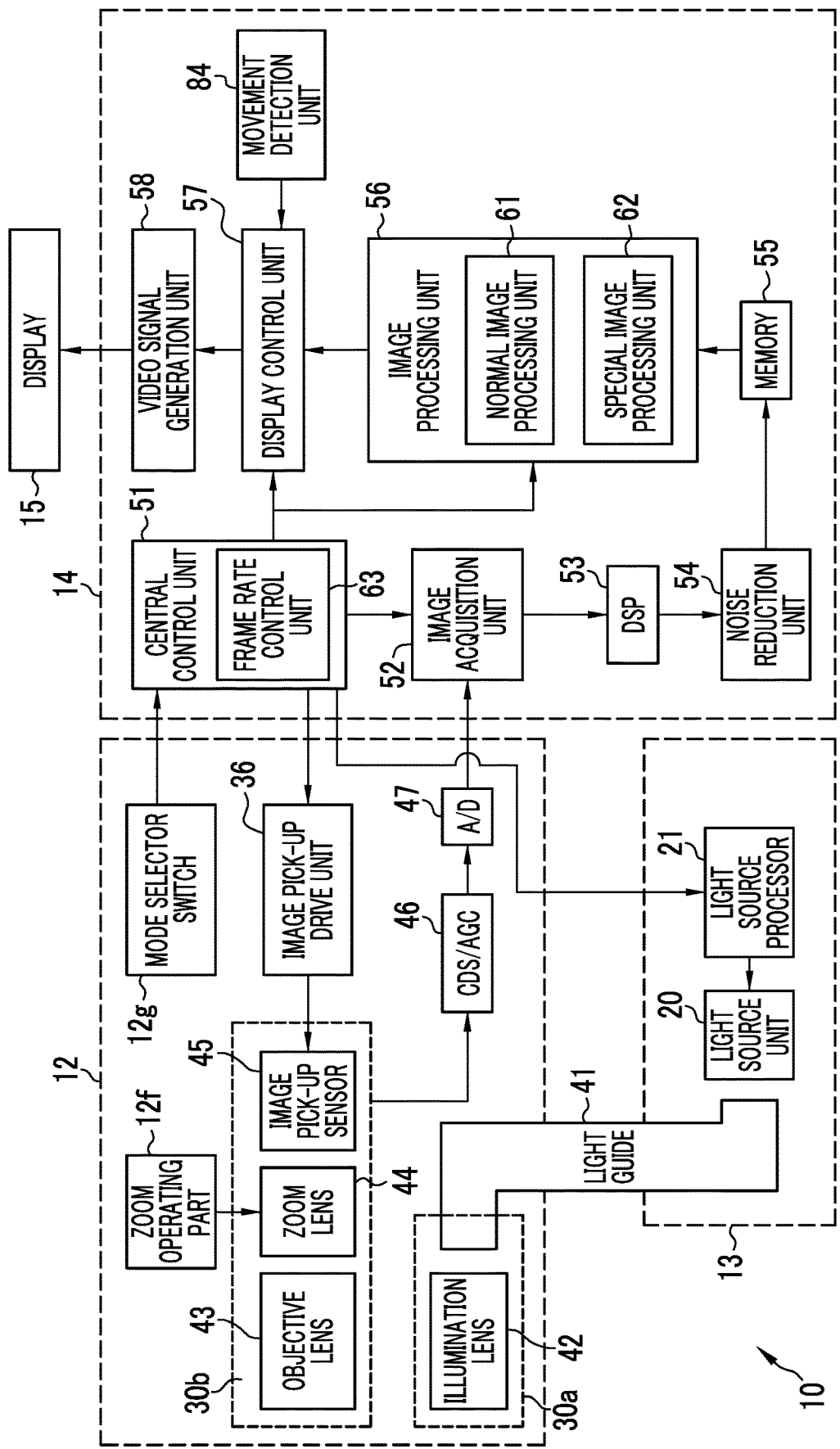
FIG. 13 is a block diagram showing a function of an endoscope system including a movement detection unit.

As shown in FIG. 13, in a case where the movement vector method is used, the processor device 14 includes a movement detection unit 84. In addition to calculating a movement vector on the basis of an endoscopic image, the movement detection unit 84 may detect relative motion between the image pick-up sensor 45 and an observation target by using a physical method such as a gyro sensor. In a case where a movement vector is calculated on the basis of an endoscopic image, the movement vector may be calculated on the basis of a shape, a blood vessel, a lesion, a structure such as a cut edge, or a landmark such as a treatment tool captured in the endoscopic image.

In the method of generating an interpolation frame according to the duplication method, a past endoscopic image captured may be duplicated to generate a display image, and this display image may be used as an interpolation frame. The endoscopic image to be duplicated may be an endoscopic image captured immediately before, or an endoscopic image captured in the past other than immediately before may be used. In the addition averaging method, in a case where a ratio of the two immediately preceding endoscopic images is set to 100:0, this is the same as generating an interpolation frame by duplicating the endoscopic images captured two before, and in a case where the ratio is set to 0:100, this is the same as generating an interpolation frame by duplicating one endoscopic image captured immediately before. An endoscopic image to be duplicated may be generated by duplicating one interpolation frame or by duplicating two or more interpolation frames according to a relationship between the imaging frame rate and the display frame rate included the condition.

By using the above method, a display frame rate can be adjusted by the display image generation unit 74 generating a display image in response to an instruction from the frame rate adjustment unit 71. The past endoscopic image used in a case where the display image generation unit 74 generates the interpolation frame 83 as a display image is one or two or more frames immediately before a timing of generating the interpolation frame 83. However, in some cases, the number of frames may be three or more. Endoscopic images captured in the past, which are temporally separated, may be used instead of two consecutive frames captured immediately before the generation of the interpolation frame 83.

The display image generated by the display control unit 57 is generated as a video signal to be displayed on the display 15 by the video signal generation unit 58, and is sent to the display 15. The display 15 displays a display image sent from the video signal generation unit 58.

As a method of displaying the display image in the first observation mode, in a case where two types of endoscopic images such as a display image based on the first image 81 and a display image based on the second image 82 are displayed, the endoscopic images may be displayed on the same display 15 or may be respectively displayed on different displays. Since the display image based on the first image 81 is adjusted to have a display frame rate higher than an imaging frame rate and is thus displayed smoothly, the first image 81 and the second image 82 may be displayed with different display areas, such as the display image based on the first image 81 being displayed with a display area larger than a display area of the display image based on the second image 82.

Figure 14:
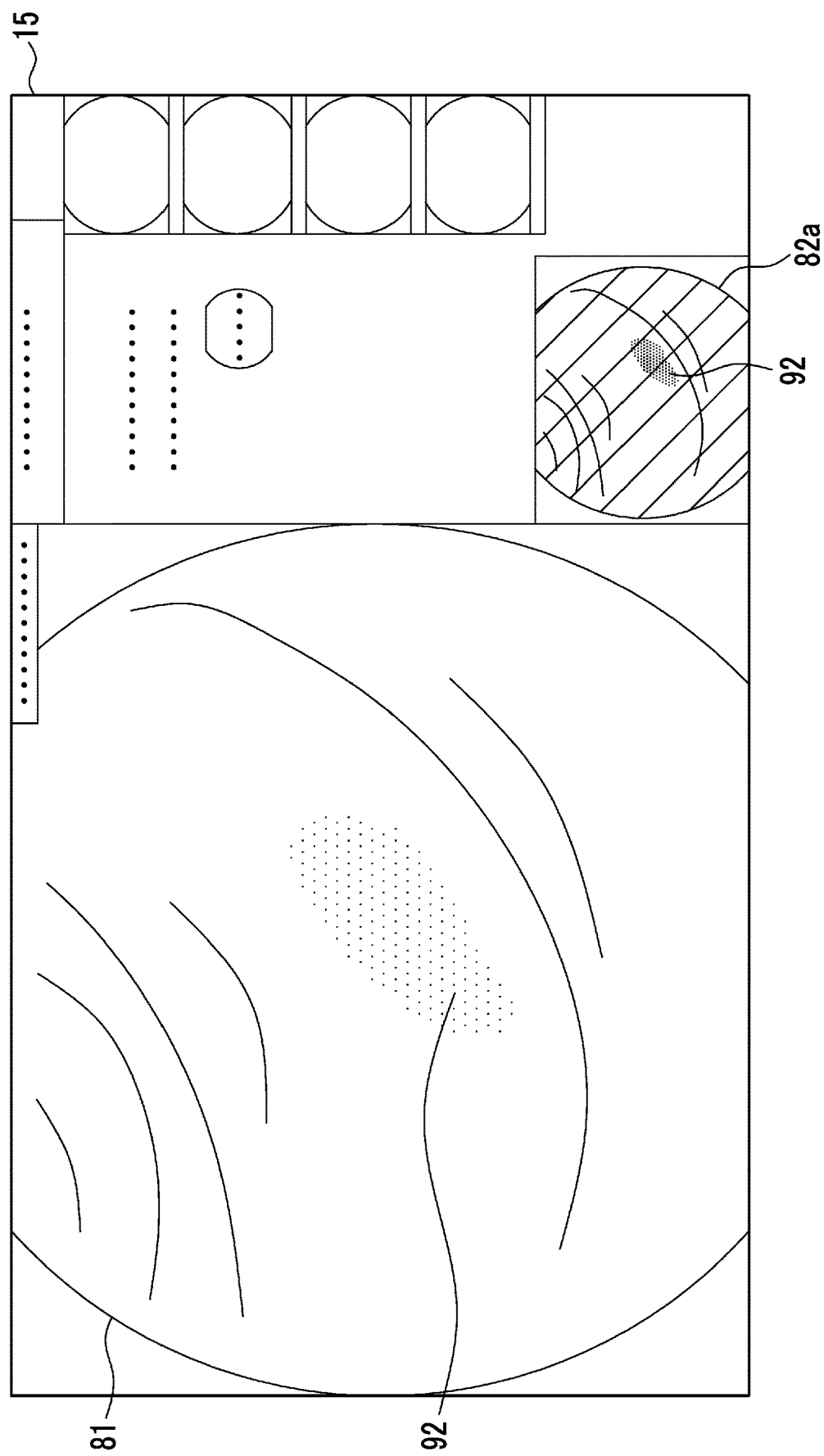
FIG. 14 is an image diagram of a display that displays a first image and a second image that undergoes a color difference expansion process.

As shown in FIG. 14, in the first observation mode, in a case where a second image 82a subjected to the color difference expansion process is displayed as the first image 81 and the second image 82, the first image 81 is displayed in a large area region of the display 15, 81 is displayed, and the second image 82a is displayed in a small area region thereof. The first image 81 is an image having a natural hue due to white light, and is thus an image familiar to, for example, a doctor performing an examination. Therefore, since the first display frame rate of the first image 81 is adjusted to be higher than the first imaging frame rate, the first image 81 is smooth and easy to view, and even in a case where the first image 81 is displayed in a large area region, the first image 81 can be viewed without discomfort. In FIG. 14, the observation target captured in the first image 81 and the second image 82a has redness 92.

Since the second image 82a is an image in which a structure of a superficial blood vessel or the like is emphasized and displayed due to the special light and the color enhancement process, a lesion or the like in which blood vessels are dense is emphasized and displayed. Therefore, even in a case where the second image 82a is displayed in a region having a relatively small area, the lesion or the like is emphasized and displayed. Therefore, by displaying the second image 82a side by side with the first image 81, it is possible to prevent the lesion or the like from being overlooked.

In the first observation mode, the first image 81 may be displayed and a second image 82b subjected to pseudo-color processing may be displayed. In a case where the second image 82b is displayed, an image analysis result screen 91 using the second image 82b may be further displayed.

Figure 15:
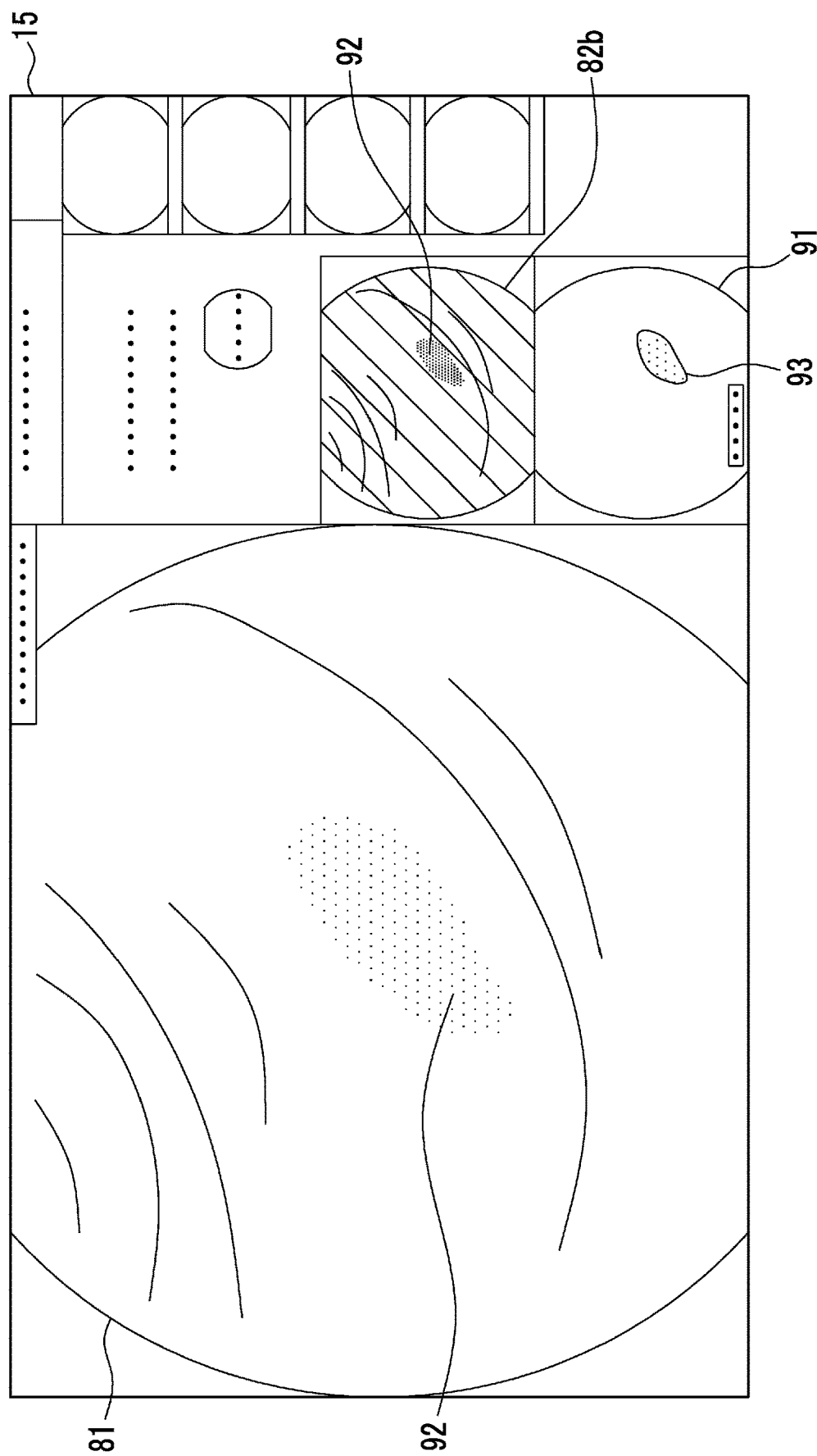
FIG. 15 is an image diagram of a display that displays a first image, a second image that undergoes pseudo-color processing, and an image analysis result.

As shown in FIG. 15, for example, in the first observation mode, the first image 81 is displayed in a large area region of the display 15, and the second image 82b subjected to pseudo-color processing and the image analysis result screen 91 using the second image 82b are displayed in a small area region thereof. The redness 92 included in the second image 82b is subjected to image analysis using artificial intelligence (AI) and/or image analysis for physical quantity measurement such as measurement of an oxygen saturation or a distance, and the result is shown as, for example, a lesion region 93 on the image analysis result screen 91. Therefore, a doctor will proceed with the observation with the easy-to-view first image 81 of which a display frame rate is adjusted by using white light, and diagnosis can be performed while immediately obtaining information regarding diagnosis of whether the redness 92 is, for example, neoplastic or non-neoplastic from the image analysis result screen 91. An image subjected to be image analysis may be any kind of acquired endoscopic image, and may be, for example, one or more of the first image, the second image, and/or the third image. In this case, the image analysis may be performed at the same time, or may be performed in parallel by different image analysis units. The image analysis may be performed by using a device other than the processor device 14. As described above, since it is possible to acquire an appropriate type of endoscopic image according to various image analyses and use it for each image analysis, the accuracy of the image analysis can be improved.

Figure 16:
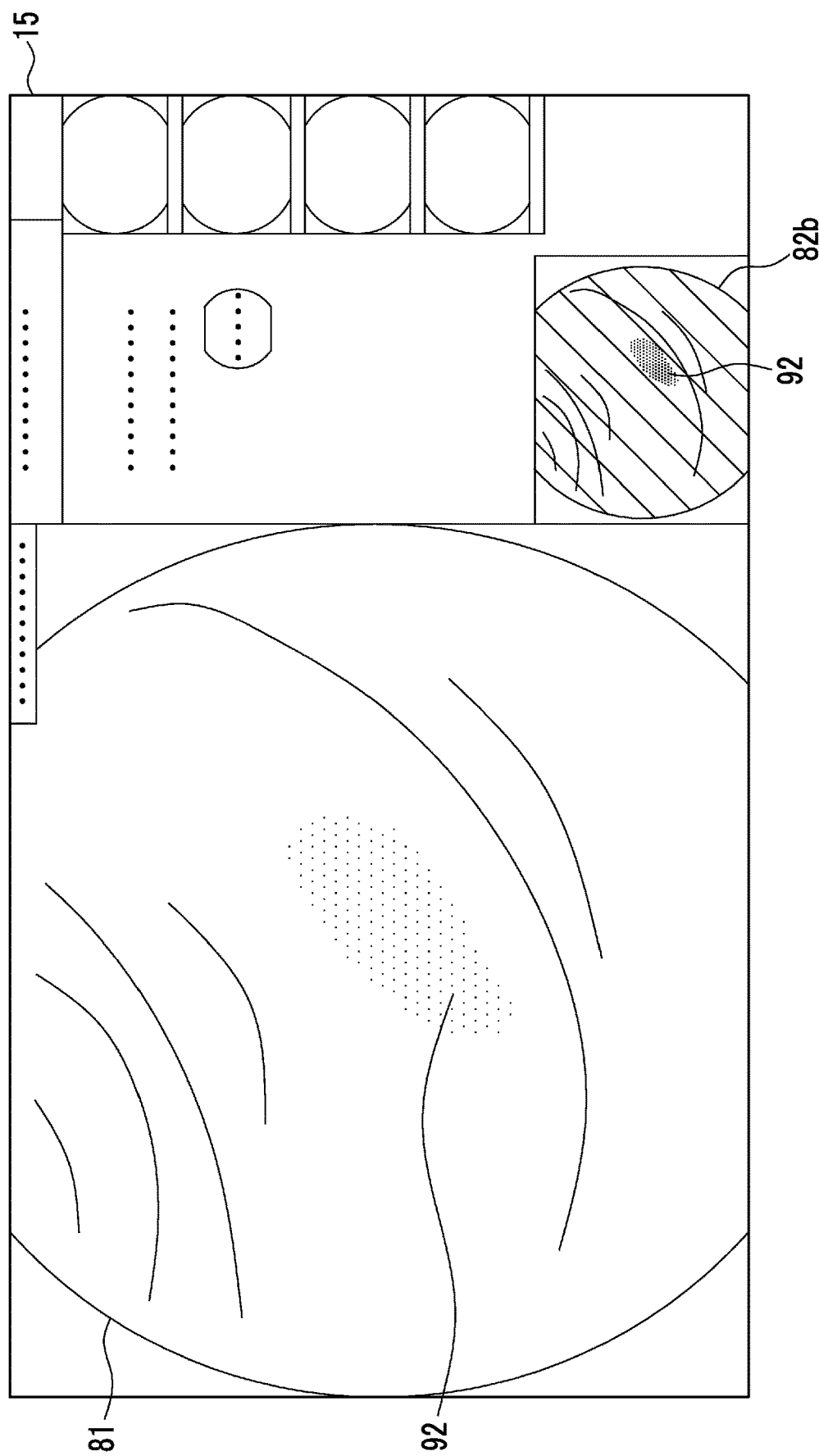
FIG. 16 is an image diagram of a display that displays a first image and a second image that undergoes pseudo-color processing.

As shown in FIG. 16, in the first observation mode, the first image 81 may be displayed in the large area region of the display 15, and only the second image 82b subjected to pseudo-color processing may be displayed in the small area region thereof. In the first observation mode, in a case where the first image 81 is displayed and the second image 82 is not displayed, the first image 81 in the large area region of the display 15 may be displayed, and nothing may be displayed or an image other than the second image 82 may be displayed in the small area region. The first image 81 may be displayed in the small area region, and the second image 82 may be displayed in the large area region. The second image 82 is a general term for the second image, and includes the second image 82a and the second image 82b.

Figure 17:
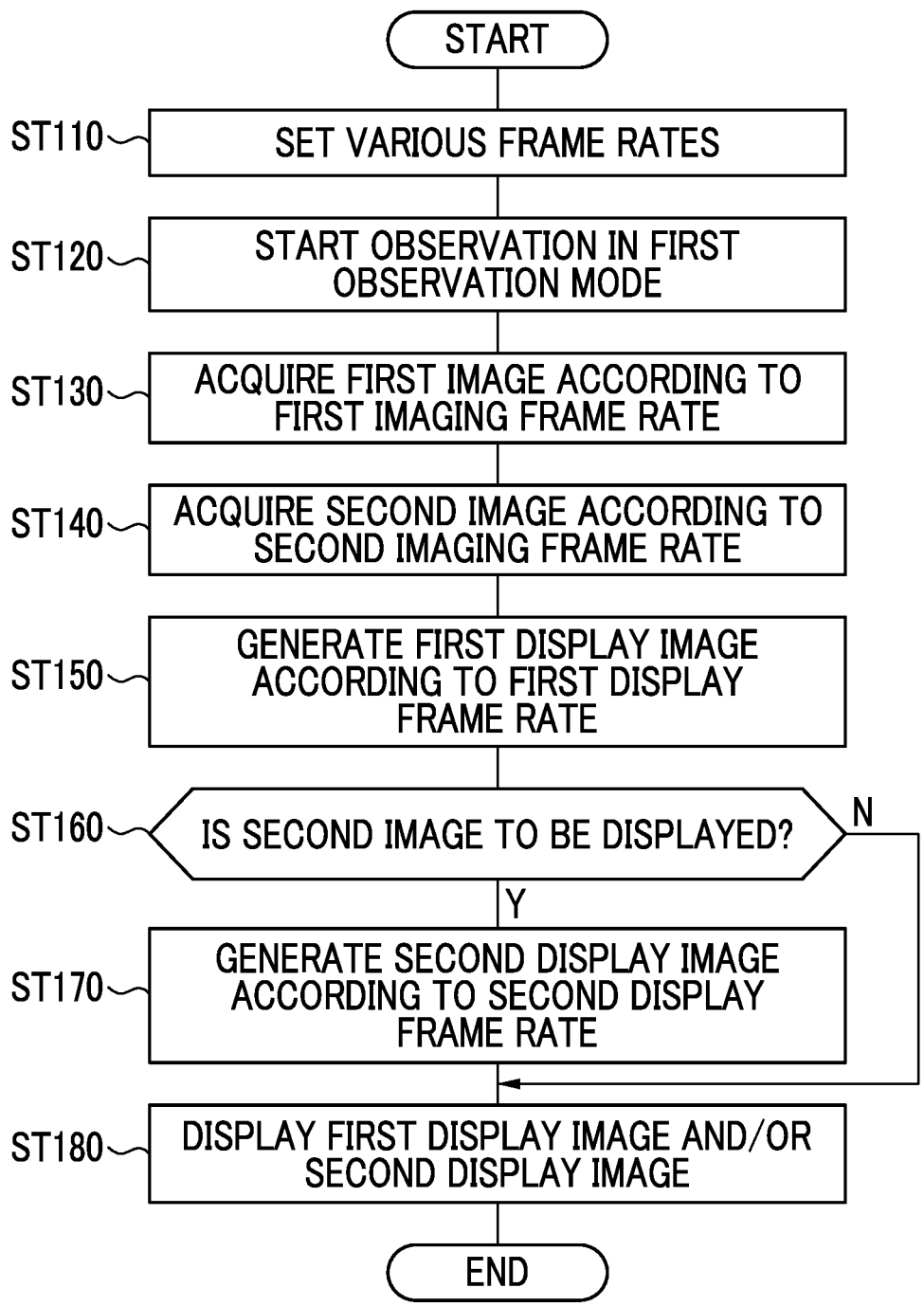
FIG. 17 is a flowchart showing a series of flows of an operation of the endoscope system in a first observation mode.

Next, a series of flows of an operation of the endoscope system of the present embodiment in the first observation mode will be described with reference to a flowchart of FIG. 17. Endoscopy is started in the first observation mode, and various frame rates are set (step ST110). The frame rates set in the first observation mode are the first imaging frame rate and the first display frame rate of the first image 81, and the second imaging frame rate and the second display frame rate of the second image 82. After setting various frame rates, observation in the first observation mode is started (step ST120). Illumination light is applied to an observation target according to the pattern P1, and the first image 81 is first acquired. The first image 81 is acquired according to the first imaging frame rate (step ST130).

Next, the second image 82 is acquired according to the second imaging frame rate (step ST140). After the first image 81 is acquired, a first display image is generated according to the first display frame rate (step ST150). In a case where the second image 82 is displayed (Y in step ST160), a second display image is generated according to the second display frame rate (step ST170). Next, the generated first display image and second display image are displayed on the display 15. In a case where the second image 82 is not displayed (N in step ST160), the first display image is displayed.

Since the endoscope system 10 is configured as described above, even in a case where two types of endoscopic images are acquired, a display frame of the first image 81 is adjusted such that deterioration in the image quality of the first image 81 is suppressed at the time of display, and it is also possible to simultaneously obtain the high-quality second image 82 in which the number of pixels is not thinned out. This can also be applied in a case where two or more types of endoscopic images are acquired, and a plurality of types of endoscopic images are acquired according to the purpose, and each endoscopic image can be acquired at image quality in accordance with a corresponding purpose. Consequently, it is possible to display two or more types of endoscopic images with less deterioration in image quality, and thus a doctor can proceed with an examination while acquiring a plurality of image analysis results by using a plurality of endoscopic images with different pieces of illumination light acquired in the examination without requiring special labor. Therefore, the doctor can proceed with diagnosis by using high-quality endoscopic images while simultaneously obtaining a plurality of image analysis results useful for the diagnosis as diagnosis support information.

The image pick-up sensor 45 is an image pick-up sensor 45 that performs an imaging operation according to a rolling shutter method in which signal reading is executed according to a sequential reading method and resetting is performed according to a sequential reset method. However, in the imaging operation using the rolling shutter method, the imaging operation may be performed according to a pseudo-global shutter method in which an exposure period is adjusted by adjusting an irradiation period that is a period for applying illumination light.

In this case, each of a plurality of pieces of illumination light may be intermittently applied under the control of the light source unit 20. Intermittent irradiation means irradiation such that a light-off period is provided before and after the irradiation period. Preferably, the irradiation is performed such that an irradiation period is included at least once in a period of one frame. Therefore, preferably, each of the irradiation period and the light-off period is included at least once in the period of one frame.

Figure 18:
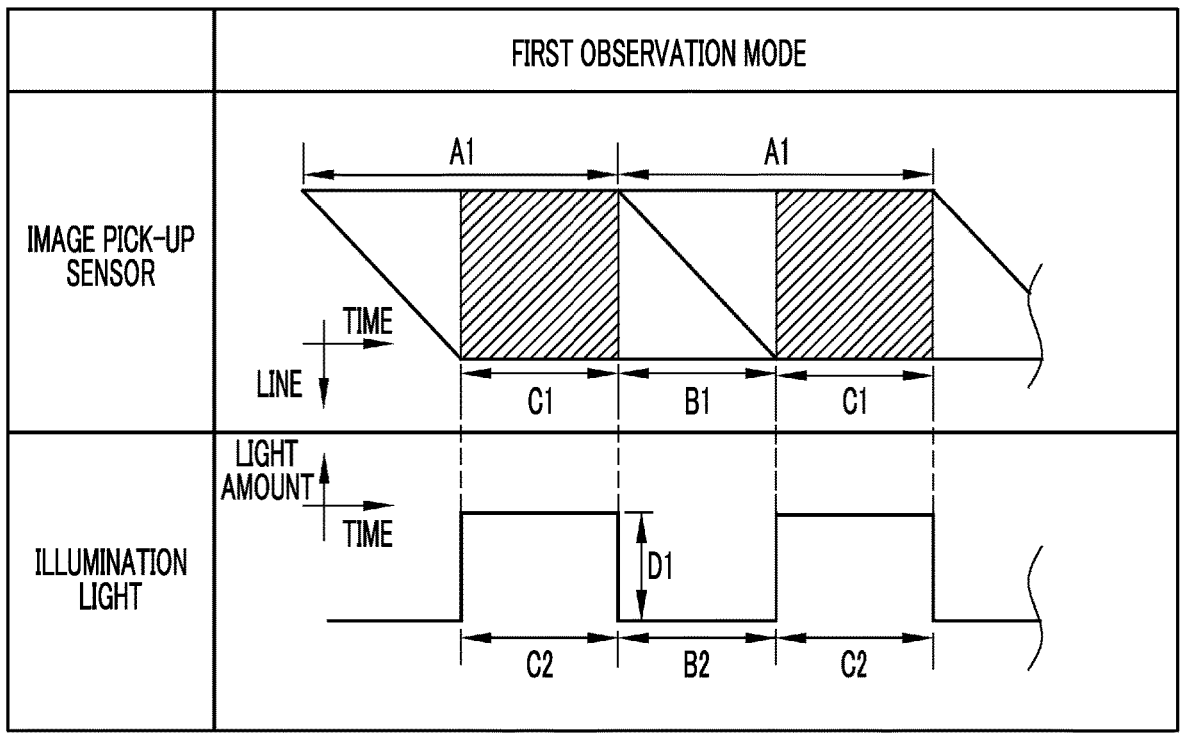
FIG. 18 is an explanatory diagram for describing a relationship between the image pick-up sensor and illumination light in the first observation mode.

As shown in FIG. 18, as a pseudo-global shutter method, illumination light is applied in an irradiation period C2, then turned off in a light-off period B2, and this is repeated. In the image pick-up sensor 45, exposure is performed in an exposure period C1 that is the same period as the irradiation period C2, and then the exposure is performed in a reading period B1 that is the same period as the light-off period B2 in which the illumination light is turned off. In FIG. 18, it is shown by diagonal lines that the pixel rows are sequentially read with the passage of time.

The illumination light is intermittently applied during the irradiation period C2 in accordance with the exposure period C1 of the image pick-up sensor. In FIG. 18, in the line of the image pick-up sensor 45, a region exposed by the illumination light is schematically shown by shading. It is preferable to employ such a pseudo-global shutter method because problems such as color mixing do not occur in a case where the illumination light is changed. An image pick-up period A1 is a period including the exposure period C1 and the reading period B1, and is a period of one frame.

Regarding an image pick-up period A1 in which the image pick-up sensor 45 performs image pick-up and the reading period B1 in which an image signal obtained through the image pick-up is read, the image pick-up period A1 is longer than the reading period B1. Consequently, an exposure period for exposing the entire line of the image pick-up sensor 45 can be provided in one frame.

For example, the image pick-up period A1 may be 1/45 sec (seconds). Each of the exposure period C1 and the reading period B1 may be set to 1/90 sec. Therefore, it can be said that an imaging frame rate in this case is 45 fps.

The light source unit 20 may apply illumination light by changing the irradiation period C2 for applying any of a plurality of pieces of illumination light. For example, the irradiation period C2 in a case of intermittently applying the illumination light is selected by a user from 1/90 sec, 1/200 sec, or 1/400 sec.

In this case, the exposure period C1 may be changed on the basis of the changed irradiation period C2. That is, a shutter speed may be controlled according to the irradiation period C2. The shutter speed controlled according to the irradiation period C2 of the illumination light may be, for example, 1/90 sec, 1/200 sec, or 1/400 sec.

In the present embodiment, the pattern P1 is repeated in which the first illumination light and the second illumination light are switched to be emitted (refer to FIG. 6), imaging is performed for two consecutive frames with the first illumination light L1, and imaging is performed for one frame by switching to the second illumination light L2. Therefore, out of 45 fps, the first image 81 based on the first illumination light L1 is acquired for 30 fps, and the second image 82 based on the second illumination light L2 is acquired for 15 fps.

A light emission amount may be calculated by using a light emission integral amount formed of the irradiation period C2 in which the light source unit 20 applies the illumination light and an instantaneous light emission amount D1 that is a light emission amount in the unit time of the illumination light. Therefore, a light emission amount of illumination light applied by the light source unit 20 in one irradiation of the illumination light can be controlled.

A light emission amount may be controlled according to automatic power control (APC), and in this case as well, the light emission amount may be calculated by using a light emission integral amount formed of the irradiation period C2 in which the light source unit 20 applies the illumination light and the instantaneous light emission amount D1 that is a light emission amount in the unit time of the illumination light, and may be controlled by using the irradiation period C2 and/or the instantaneous light emission amount D1 of the illumination light. A photometer or the like (not shown) may be used to acquire the instantaneous light emission amount D1.

As described above, the endoscope system 10 may include a second observation mode to which the first observation mode can be switched. In the second observation mode, an observation target is observed in the same illumination light without switching of illumination light. In the second observation mode, the observation target is irradiated with third illumination light included in a plurality of pieces of illumination light, and the image pick-up sensor 45 is controlled such that the observation target is imaged according to a preset third imaging frame rate during a third period in which the third illumination light is applied. The image pick-up sensor 45 acquires a third image captured in the third period. In a case where the third image is displayed on the display, it is preferable to display the third image according to a third display frame rate that is equal to or lower than the third imaging frame rate. The third imaging frame rate is a frame rate for capturing an image while applying the third illumination light, and the third display frame rate is a frame rate for displaying the third image on the display 15.

In the second observation mode, since the third image is displayed according to the third display frame rate that is equal to or lower than the third imaging frame rate, no interpolation frame is generated. Therefore, in the second observation mode, a display image is not generated.

Figure 19:
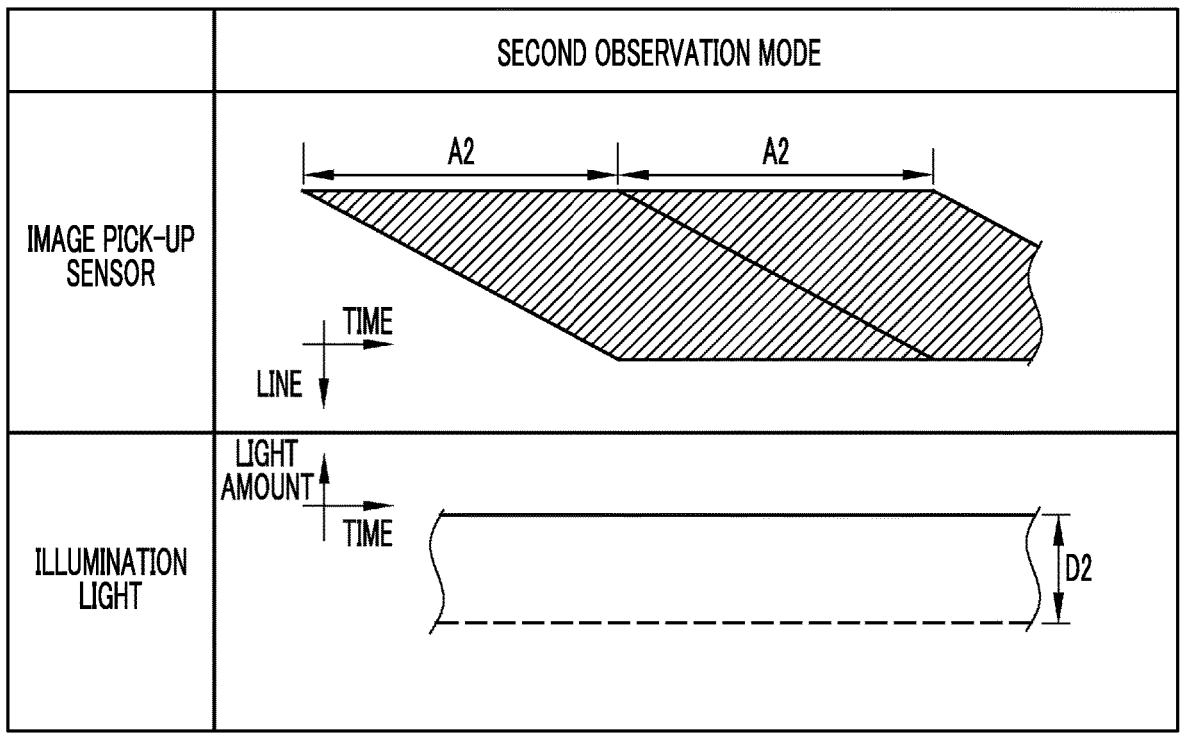
FIG. 19 is an explanatory diagram for describing a relationship between the image pick-up sensor and illumination light in a second observation mode.

In the second observation mode, the image pick-up sensor 45 performs an image pick-up operation according to a rolling shutter method. As shown in FIG. 19, as the rolling shutter method, the illumination light is constantly applied. In the image pick-up sensor 45, constant exposure is performed, and pixel rows are sequentially read with the passage of time. A period A2 in which reading after exposure is completed from the first pixel row to the last pixel row is one frame. For example, the image pick-up period A2 may be 1/60 sec. Therefore, the imaging frame rate in this case is 60 fps.

In the second observation mode, since the image pick-up sensor 45 performs an image pick-up operation according to the rolling shutter method as described above, the image pick-up period A2 in which the image pick-up sensor 45 captures an image is a period including an exposure period and a reading period in which an image signal obtained through the image pick-up is read and is a period of one frame. In the present embodiment, the period of one frame that is the image pick-up period A2 is 1/60 sec.

In the second observation mode, since the illumination light is always turned on, an amount of light can be controlled by using the light emission amount D2 of the illumination light. In the same manner as in the first observation mode, the light emission amount D2 may be controlled according to the APC, and in this case as well, an amount of light may be controlled by using the light emission amount D2 of the illumination light. A shutter speed may be controlled according to the image pick-up period A2 of the image pick-up sensor 45.

In the present embodiment, in the second observation mode, the third imaging frame rate based on the third illumination light may be, for example, 60 fps. The third display frame rate is equal to or lower than the third imaging frame rate, and may be, for example, 60 fps, 50 fps, or 59.94 fps.

In the above embodiment, the present invention is applied to the case of processing an endoscopic image, but is also applicable to a processor device, a medical image processing device, a medical image processing system, or the like processing a medical image other than an endoscopic image.

In the present embodiment, in the first observation mode, two types of images such as the first image and the second image are acquired, but three or more types of images may be acquired. In the first observation mode, a tumor and a non-tumor are distinguished from each other through image analysis using AI for the second image, and the result is displayed on the display 15, but image analysis may be performed by using any of a plurality of types of acquired images, or image analysis may be performed on a generated image such as an interpolation frame. That is, image analysis may be performed on one or two or more of three types of endoscopic images such as the first image, the interpolation frame based on the first image, and the second image.

As described above, in one or more types of endoscopic images among the plurality of types of acquired images, analysis based on image information, for example, acquisition of diagnostic support information using AI, or acquisition of physical quantity measurement information such as measurement of an oxygen saturation or a distance in a subject may be performed. As the endoscopic image used for image analysis, the type of endoscopic image from which favorable analysis results can be obtained may be selected and used depending on the type of image analysis. In this case, a plurality of analyses may be performed simultaneously or in parallel.

For example, in the first observation mode, the first image that is a normal image, the second image that is a special image, and the third image that is a special image different from the second image are acquired, an oxygen saturation of a subject is calculated by performing analysis by using the first image and the second image, a lesion of the subject is detected by performing another analysis by using the second image, and diagnostic information regarding the malignancy of the detected lesion can be acquired by performing still another analysis by using the third image. As described above, by performing different image analysis processes by using a plurality of types of endoscopic images, it is possible to automatically obtain a plurality of pieces of diagnostic information during observation using the endoscope.

The analysis may be performed in the processor device 14 or may be performed by using another device. For example, in a case of performing a plurality of analyses, the analyses may be performed by an image processing device (not shown) connected to the processor device 14. Regarding an analysis result, the display 15 may be connected to the image processing device, and the image processing device may perform control for displaying the analysis result on the display 15. In this case, endoscopic images such as the first image 81, the second image 82, and/or the interpolation frame 83 to be displayed on the display 15 may be sent from the processor device 14 to the image processing device, and the image processing device may perform control for displaying these images and an analysis result on the display 15.

In a case of displaying an endoscopic image and/or an analysis result, the endoscopic image and/or the analysis result may be displayed on a plurality of displays 15 or on a small portable terminal device such as a tablet terminal (not shown). At the time of display, the layout of the screen and the like can be set in advance according to the device to be displayed.

In the present embodiment, hardware structures of processing units executing various processes, such as the central control unit 51, the image acquisition unit 52, the DSP 53, the noise reduction unit 54, the image processing unit 56, the display control unit 57, and the video signal generation unit 58 included in the processor device 14 are various processors as described below. The various processors include a programmable logic device (PLD), that is a processor of which a circuit configuration can be changed after manufacturing, such as a central processing unit (CPU) or a field programmable gate array (FPGA) that is a general-purpose processor that executes software (programs) and functions as various processing units, a dedicated electric circuit that is a processor having a circuit configuration specially designed to execute various processes, and the like.

One processing unit may be configured with one of these various processors, or may be configured with a combination of two or more processors of the same type or different types (for example, a plurality of FPGAs or a combination of a CPU and an FPGA). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined.

EXPLANATION OF REFERENCES

10: endoscope system
12: endoscope
12*a*: insertion part
12*b*: operating part
12*c*: bendable part
12*d*: tip part
12*e*: angle knob
12*f*: zoom operating part
12*g*: mode selector switch
12*h*: forceps port
12*i*: freeze switch
13: light source device
14: processor device
15: display
16: keyboard
20: light source unit
20*a*: V-LED
20*b*: B-LED
20*c*: G-LED
20*d*: R-LED
21: light source processor
30*a*: illumination optical system
30*b*: image pick-up optical system
36 image pick-up drive unit
38: pixel
39: color filter array
39*a*: blue filter
39*b*: green filter
39*c*: red filter
41: light guide
42: illumination lens
43 objective lens
44 zoom lens
45: image pick-up sensor
45*a*: image pick-up surface
46: CDS/AGC circuit
47: A/D converter
51: central control unit
52: image acquisition unit
53: DSP
54: noise reduction unit
55: memory
56: image processing unit
57: display control unit
58: video signal generation unit
61: normal image processing unit
62: special image processing unit
63: frame rate control unit
71: frame rate adjustment unit
72: imaging frame rate control unit
73: display frame rate control unit
74: display image generation unit
81: first image
82, 82*a*, 82*b*: second image
83: interpolation frame
84: movement detection unit
91: image analysis result screen
92: redness
93: lesion region
A1, A2: image pick-up period
B1: reading period
B2: light-off period
C1: exposure period
C2: irradiation period
D1: instantaneous light emission amount
D2: light emission amount
E1, E2: range
L1: first illumination light
L2: second illumination light
P1: pattern
X: row direction
Y: column direction
ST110 to ST180: step

What is claimed is:

1. An endoscope system comprising:
an endoscope that includes an image pick-up sensor;
a light source that irradiates a subject with each of a plurality of pieces of illumination light having different spectra; and
a processor device that includes a processor, wherein the processor is configured to perform followings in a first observation mode:

controlling the light source such that the subject is irradiated with each of the plurality of pieces of illumination light in a preset order;

controlling the image pick-up sensor such that the subject is imaged according to a preset first imaging frame rate during a first period in which first illumination light included in the plurality of pieces of illumination light is applied;

acquiring a first image captured by the image pick-up sensor during the first period;

generating an interpolation frame in which the first image is changed, by performing frame interpolation on the basis of the first image;

generating a first display image according to a first display frame rate higher than the first imaging frame rate, by performing frame interpolation on the basis of the first image by combining the first image and the interpolation frame, wherein in the first display image, the interpolation frame is disposed between two of the first images in a time series; and displaying the first display image on a display.

2. The endoscope system according to claim 1, wherein the processor is configured to perform followings in the first observation mode:

controlling the image pick-up sensor such that the subject is imaged according to a preset second imaging frame rate during a second period in which second illumination light included in the plurality of pieces of illumination light is applied; and acquiring a second image captured by the image pick-up sensor during the second period.

3. The endoscope system according to claim 2, wherein the processor is configured to perform control for displaying the second image on the display.

4. The endoscope system according to claim 3, wherein the processor is configured to control the light source such that the subject is irradiated with the first illumination light or the second illumination light by repeating a pattern including the first illumination light and the second illumination light.

5. The endoscope system according to claim 4, wherein the processor is configured to generate a second display image according to a second display frame rate lower than the second imaging frame rate on the basis of the second image.

6. The endoscope system according to claim 1, wherein the processor is configured to control the light source such that the subject is repeatedly irradiated with a pattern including each of the plurality of pieces of illumination light.

7. The endoscope system according to claim 1, wherein the processor is configured to control the light source such that each of the plurality of pieces of illumination light is intermittently applied.

8. The endoscope system according to claim 1, wherein the processor is configured to control the image pick-up sensor such that, in a period of one frame including an image pick-up period in which the image pick-up sensor performs image pick-up and a reading period in which an image signal obtained through the image pick-up is read, the image pick-up period is longer than the reading period.

9. The endoscope system according to claim 8, wherein the processor is configured to control the light source such that any of the plurality of pieces of illumination light is turned off and applied at least once during the image pick-up period.

10. The endoscope system according to claim 9, wherein the processor is configured to control the light source such that an irradiation period in which any of the plurality of pieces of illumination light is applied is changed and the illumination light is applied.

11. The endoscope system according to claim 10, wherein the processor is configured to control the image pick-up sensor such that an exposure period is changed on the basis of the changed irradiation period.

12. The endoscope system according to claim 1, wherein the processor is configured to control a light emission amount of the illumination light applied by the light source in one irradiation.

13. The endoscope system according to claim 12, wherein the light emission amount is calculated on the basis of an irradiation period in which the light source applies the illumination light and an instantaneous light emission amount that is a light emission amount in a unit time of the illumination light.

14. The endoscope according to claim 1, wherein the processor is configured to perform followings in a second observation mode that is switchable from the first observation mode:

controlling the light source such that the subject is irradiated with third illumination light included in the plurality of pieces of illumination light;

controlling the image pick-up sensor such that the subject is imaged according to a preset third imaging frame rate during a third period in which the third illumination light is applied;

acquiring a third image captured by the image pick-up sensor during the third period; and in a case where the third image is displayed on the display, generating a third display image according to a third display frame rate that is equal to or lower than the third imaging frame rate.

15. An operation method for an endoscope system including an endoscope that includes an image pick-up sensor, a light source that irradiates a subject with each of a plurality of pieces of illumination light having different spectra, and a processor device that includes a processor, the operation method comprising:

causing the processor in a first observation mode to execute:

a step of controlling the light source such that the subject is irradiated with each of the plurality of pieces of illumination light in a preset order;

a step of controlling the image pick-up sensor such that the subject is imaged according to a preset first imaging frame rate during a first period in which first illumination light included in the plurality of pieces of illumination light is applied;

a step of acquiring a first image captured by the image pick-up sensor during the first period;

a step of generating an interpolation frame in which the first image is changed, by performing frame interpolation on the basis of the first image;

a step of generating a first display image according to a first display frame rate higher than the first imaging frame rate, by performing frame interpolation on the basis of the first image by combining the first image and the interpolation frame, wherein in the first display image, the interpolation frame is disposed between two of the first images in a time series; and a step of performing control for displaying the first display image on a display.

\* \* \* \* \*